US012576117B2

(12) United States Patent
Kitazawa et al.

(10) Patent No.: US 12,576,117 B2
(45) Date of Patent: Mar. 17, 2026

(54) ANTIVIRAL AGENT

(71) Applicant: TOHOKU UNIVERSITY, Miyagi (JP)

(72) Inventors: Haruki Kitazawa, Miyagi (JP);
Hisashi Aso, Miyagi (JP); **Wakako
Ohtsubo**, Miyagi (JP)

(73) Assignee: TOHOKU UNIVERSITY, Miyagi (JP)

( * ) Notice: Subject to any disclaimer, the term of this
patent is extended or adjusted under 35
U.S.C. 154(b) by 483 days.

(21) Appl. No.: 17/925,333

(22) PCT Filed: May 28, 2021

(86) PCT No.: PCT/JP2021/020382
§ 371 (c)(1),
(2) Date: Nov. 15, 2022

(87) PCT Pub. No.: WO2021/241728
PCT Pub. Date: Dec. 2, 2021

(65) Prior Publication Data
US 2023/0263845 A1 Aug. 24, 2023

(30) Foreign Application Priority Data

May 29, 2020 (JP) ................................. 2020-093820

(51) Int. Cl.
| | |
|---|---|
| *A61K 35/747* | (2015.01) |
| *A61K 9/00* | (2006.01) |
| *A61P 31/14* | (2006.01) |
| *C12N 1/20* | (2006.01) |
| *C12N 1/205* | (2026.01) |
| *C12R 1/225* | (2006.01) |
| *C12R 1/25* | (2006.01) |
| *C12N 15/113* | (2010.01) |

(52) U.S. Cl.
CPC .......... *A61K 35/747* (2013.01); *A61K 9/0056*
(2013.01); *A61P 31/14* (2018.01); *C12N 1/205*
(2021.05); *C12R 2001/225* (2021.05); *C12R
2001/25* (2021.05)

(58) Field of Classification Search
CPC ................ A61K 35/747; A61K 9/0056; A61K
2035/115; A61P 31/14; A61P 31/12;
C12N 1/205; C12N 15/113; C12N 1/20;
C12R 2001/25; C12R 2001/225; A23V
2002/00; A23K 10/18; Y02A 50/30;
A23L 33/135
See application file for complete search history.

(56) References Cited

U.S. PATENT DOCUMENTS

2021/0332323 A1* 10/2021 Kim .......................... C12N 1/20

FOREIGN PATENT DOCUMENTS

| | | | | |
|---|---|---|---|---|
| KR | 101978455 B1 * | 5/2019 | ............. | A23K 10/16 |
| WO | WO-2005086870 A2 * | 9/2005 | ........... | A61K 35/747 |
| WO | WO-2015088227 A1 * | 6/2015 | ............. | A61K 35/74 |

OTHER PUBLICATIONS

Kumar, R. V. J. et al., "Putative probiotic *Lactobacillus* spp. from porcine gastrointestinal tract inhibit transmissible gastroenteritis coronavirus and enteric bacterial pathogens", Trop. Anim. Health Prod., 2010, vol. 42, pp. 1855-1860. DOI: 10.1007/s11250-010-9648-5 (Year: 2010).*
Machine Generated English Translation of WO-2015088227-A1. From Espacenet. Originally Published Jun. 18, 2015 (Year: 2015).*
Arena et al. "Immunobiosis and probiosis: antimicrobial activity of lactic acid bacteria with a focus on their antiviral and antifungal properties." Applied microbiology and biotechnology 102 (2018): 9949-9958. (Year: 2018).*
Machine Generated English Translation of KR-101978455-B1. From Espacenet. Original Published May 14, 2019 (Year: 2019).*
Albarracin et al., ("Efficient Selection of New Immunobiotic Strains With Antiviral Effects in Local and Distal Mucosal Sites by Using Porcine Intestinal Epitheliocytes", Frontiers in Immunology, vol. 11, Apr. 8, 2020 (Year: 2020).*
GenBank Accession No. GU357500, first available Feb. 9, 2010; accessed Feb. 11, 2025, 2 pages. (Year: 2010).*
GenBank Accession No. CP029616.1 (locus_tag="LS1_00398"; product="16S ribosomal RNA"), first available Sep. 24, 2018; accessed Jul. 8, 2025, 2 pages. (Year: 2018).*
Masumizu et al., Isolation and Immunocharacterization of *Lactobacillus salivarius* from the Intestine of Wakame-Fed Pigs to Develop Novel "Immunosynbiotics", Microorganisms, vol. 7(6), 167, Jun. 6, 2019 (Jun. 6, 2019), 17 pages, DOI: 10.3390/microorganisms7060167 (Year: 2019).*
Albarracin, Leonardo "Efficient Selection of New Immunobiotic Strains With Antiviral Effects in Local and Distal Mucosal Sites by Using Porcine Intestinal Epitheliocytes", Frontiers in Immunology, vol. 11, Apr. 8, 2020 (Apr. 8, 2020).
Johnson, Jethro S., et al. "Evaluation of 16S rRNA gene sequencing for species and strain-level microbiome analysis." Nature communications 10.1 (2019): 5029.
Villena, Julio "Draft Genome Sequence of *Lactobacillus plantarum* MPL16, a Wakame—Utilizing Immunobiotic Strain Isolated from Swine Feces", Genome Announcements, vol. 5, No. 10, Mar. 9, 2017 (Mar. 9, 2017).
Kumar, R. V. J. et al., "Putative probiotic *Lactobacillus* spp. from porcine gastrointestinal tract inhibit transmissible gastroenteritis coronavirus and enteric bacterial pathogens", Trop. Anim. Health Prod., 2010, vol. 42, pp. 1855-1860.

(Continued)

*Primary Examiner* — Aaron J Kosar
*Assistant Examiner* — Andrew T Moehlman
(74) *Attorney, Agent, or Firm* — Edwin S. Flores; Daniel J. Chalker; Chalker Flores, LLP

(57) ABSTRACT

A problem of the invention is to provide an antiviral agent containing as an active ingredient a probiotic which effectively exhibits an antiviral effect also on combined infection with a virus and a pathogenic bacterium. An agent containing one, two or more *Lactobacillus* strains which have 16S rRNA gene having an identity of at least 90% with the nucleotide sequence of SEQ ID NO: 1 and which have the action of enhancing the expression of an antiviral factor and/or the action of reducing the expression of a downregulator of an antiviral factor is used as an antiviral agent.

12 Claims, 13 Drawing Sheets

Specification includes a Sequence Listing.

(56)           References Cited

OTHER PUBLICATIONS

Masumizu, Y. et al., Isolation and immunocharacterization of *Lactobacillus salivarius* from the intestine of wakame-fed pigs to develop novel "immunosynbiotics", Microorganisms, 2019, vol. 7, 167.

Raftis, E.J. et al., "Unusual genome complexity in *Lactobacillus salivarius* JCM1046", BMC Genomics, 2014, 15:771.

Shimazu, T. et al., "Addition of Wakame seaweed (*Undaria pinnatifida*) stalk to animal feed enhances immune response and improves intestinal microflora in pigs", Anim. Sci. J., 2019, vol. 90, pp. 1248-1260.

Zhang, D.Y. et al., "In vitro characterisation of two *Lactobacillus* strains and evaluation of their suitability as probiotics for growing-finishing pigs", Anim. Prod. Sci., 2019, vol. 59, pp. 1537-1545.

Microorganisms—https://www.mdpi.com/2076-2607/7/6/167 dated May 22, 2020.

Animal Science Journal—https://onlinelibrary.wiley.com/doi/abs/10.1111/asj. 13274 dated May 22, 2020.

* cited by examiner

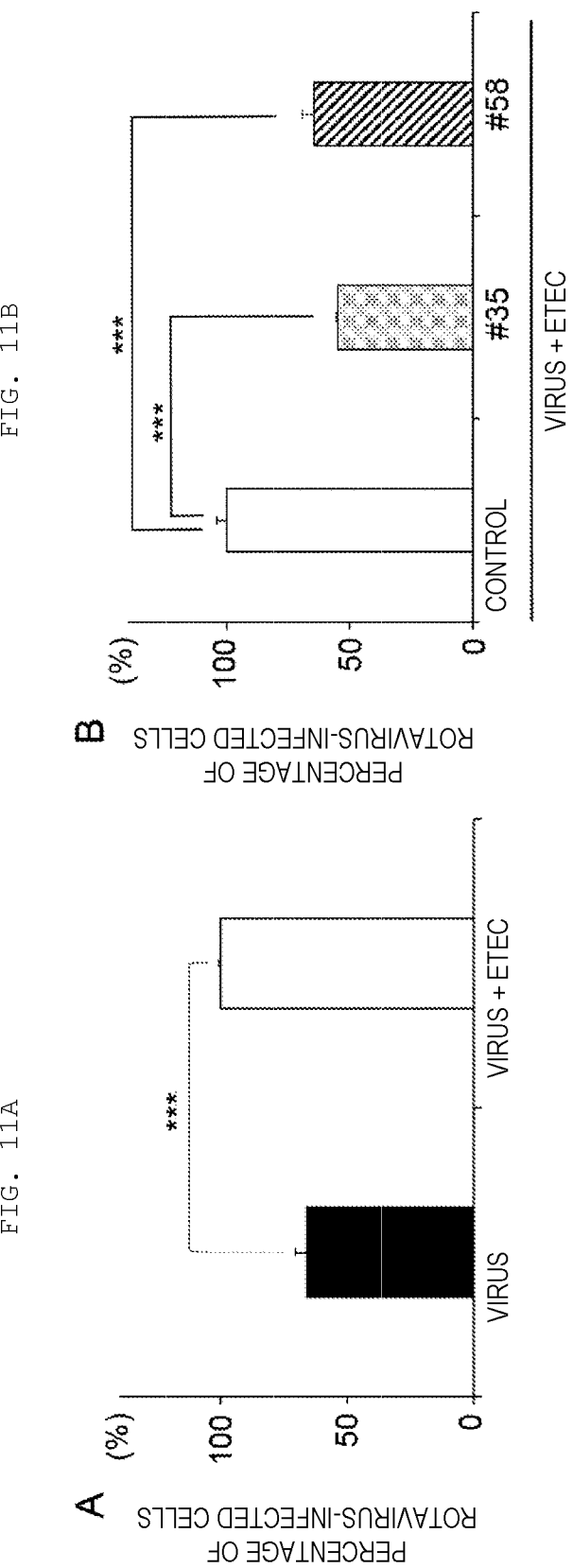

FIG. 12A
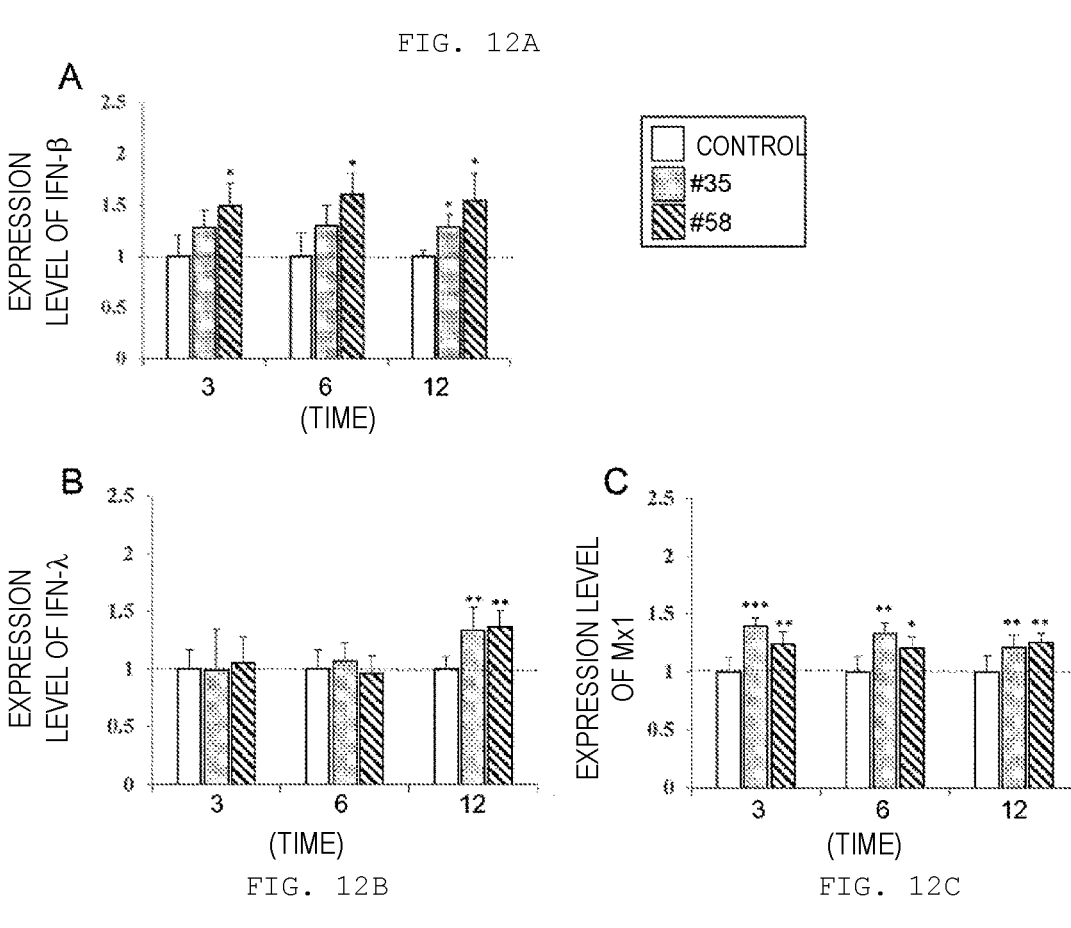
FIG. 12B
FIG. 12C
FIG. 13A
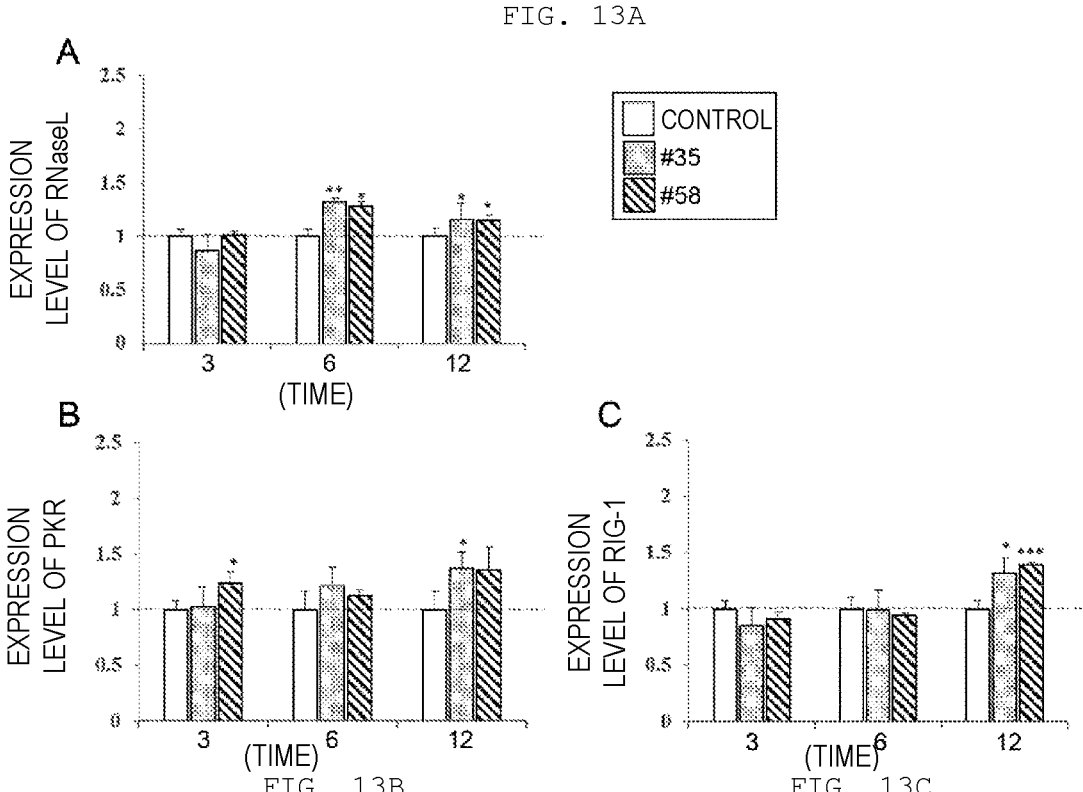
FIG. 13B
FIG. 13C

ANTIVIRAL AGENT

CROSS-REFERENCE TO RELATED APPLICATIONS

This application is the National Stage of International Application No. PCT/JP2021/020382, filed on May 28, 2021 claiming the priority of JP 2020-093820, filed on May 29, 2020, the content of each of which is incorporated by reference herein.

TECHNICAL FIELD

The present invention relates to an antiviral agent containing an antiviral probiotic (preferably, an immunobiotic [namely a probiotic having the immunomodulatory function on mucosa such as intestinal mucosa]) as an active ingredient.

INCORPORATION-BY-REFERENCE OF MATERIALS FILED ON COMPACT DISC

The present application includes a Sequence Listing which has been submitted in ASCII format via EFS-Web and is hereby incorporated by reference in its entirety. Said ASCII copy, created on Oct. 24, 2022, is named HRTA1055US_SeqList.txt and is 26 kilobytes in size.

DEPOSIT OF BIOLOGICAL MATERIAL

The following biological material has been deposited under the terms of the Budapest Treaty with the NITE Patent Microorganisms Depositary, National Institute of Technology and Evaluation, #122, 2-5-8 Kazusakamatari, Kisarazu-shi, Chiba 292-0818, Japan, and given the following number:

| Deposit | Accession Number | Date of Deposit |
| --- | --- | --- |
| Lactobacillus salivaruis FFIG35 | NITE BP-03218 | May 19, 2020 |
| Lactobacillus salivaruis FFIG58 | NITE BP-03219 | May 19, 2020 |
| Lactobacillus salivaruis FFIG71 | NITE BP-03220 | May 19, 2020 |
| Lactobacillus salivaruis FFIG131 | NITE BP-03221 | May 19, 2020 |
| Lactiplantibacillus (Lactobacillus) plantarum FFIG6ML686 | NITE BP-03466 | Apr. 23, 2021 |
| Lactiplantibacillus (Lactobacillus) plantarum FFIG6VG132 | NITE BP-03467 | Apr. 23, 2021 |
| Lactiplantibacillus (Lactobacillus) plantarum FFIG6ML6109 | NITE BP-03468 | Apr. 23, 2021 |
| Lactiplantibacillus (Lactobacillus) plantarum FFIG6VG141 | NITE BP-03469 | Apr. 23, 2021 |
| Lactiplantibacillus (Lactobacillus) plantarum FFIG2CS82 | NITE BP-03470 | Apr. 23, 2021 |
| Lactiplantibacillus (Lactobacillus) plantarum FFIG3CS123 | NITE BP-03471 | Apr. 23, 2021 |
| Lactiplantibacillus (Lactobacillus) plantarum FFIGIFeB18 | NITE BP-03472 | Apr. 23, 2021 |
| Limosilactobacillus (Lactobacillus) mucosae FFIG4FeB195 | NITE BP-03473 | Apr. 23, 2021 |
| Lactiplantibacillus (Lactobacillus) plantarum FFIG16 | NITE BP-03474 | Apr. 23, 2021 |

The strains have been deposited under conditions that assure that access to the culture will be available during the pendency of this patent application to one determined by the Commissioner of Patents and Trademarks to be entitled thereto under 37 C.F.R. § 1.14 and 35 U.S.C. § 122. The deposit represents a substantially pure culture of the deposited strain. The deposit is available as required by foreign patent laws in countries wherein counterparts of the subject application, or its progeny are filed. However, it should be understood that the availability of a deposit does not constitute a license to practice the subject invention in derogation of patent rights granted by government action.

BACKGROUND ART

Probiotics are living microorganisms which act on the normal microbiota in the body (especially in the intestinal tract) of a host mammal to improve the balance thereof and which thus provide beneficial effects on the body of the mammal. Probiotics are known to exhibit a sterilizing effect or an immunostimulatory effect on infection with a virus or a pathogenic bacterium by inducing production of a disinfecting substance, competitive intake of nutritional components, competition on the attachment site, promotion/suppression of the metabolic enzyme activity or the like.

Specific examples of known probiotics include lactic acid bacteria of the genus Lactobacillus, the genus Bifidobacterium, the genus Enterococcus, the genus Leuconostoc, the genus Pediococcus and the like. Specifically, a cytoplasm fraction of lactic acid bacterium cells and an immunostimulating composition containing a cytoplasm fraction have been reported (PTL 1). Moreover, it has been reported that lyophilized powder of Lactobacillus brevis subsp. coagulans has the action of enhancing the expression of interferon (IFN)-α and IFN-γ and the action of activating natural killer (NK) cells (PTL 2). It has also been reported that spore-forming lactic acid bacteria such as Bacillus coagulans have an antiviral effect on infection with a common cold virus or an influenza virus (PTL 3). Furthermore, it has been reported that lactic acid bacteria such as Lactobacillus plantarum, Lactobacillus rhamnosus, Lactobacillus fermentum, Lactobacillus paracasei and Lactobacillus gasseri can be used for preventing or treating viral infection (PTL 4). It has also been reported that Lactobacillus brevis subsp. coagulans and Enterococcus faecalis exhibit an excellent prophylactic effect on infection with an influenza virus when used in combination (PTL 5). However, a probiotic which effectively exhibits an antiviral effect on combined infection with a virus and a pathogenic bacterium has not been known so far.

CITATION LIST

Patent Literature

PTL 1: JP-A-5-252900
PTL 2: JP-A-6-206826
PTL 3: JP-A-2008-13543
PTL 4: JP-T-2009-511470 (The term "JP-T" as used herein means a published Japanese translation of a PCT patent application.)
PTL 5: JP-A-2012-136450

SUMMARY OF INVENTION

Technical Problem

A problem of the invention is to provide an antiviral agent containing as an active ingredient a probiotic which effectively exhibits an antiviral effect also on combined infection with a virus and a pathogenic bacterium.

Solution to Problem

The present inventors have been extensively studying to solve the above problem. In the process, the present inventors have first identified two factors (IFN-β and Mx1) as indicators for evaluating the antiviral activities of probiotics. Next, from 116 strains of *Lactobacillus salivarius* (also called "*Ligilactobacillus salivarius*") isolated from a porcine intestinal tract, *Lactobacillus* strains showing antiviral activity have been selected using the expression levels of the two factors as indicators. Moreover, it has been found that the selected antiviral *Lactobacillus* strains have the action of enhancing the expression of antiviral factors and the action of reducing the expression of downregulators of an antiviral factor and effectively exhibit an antiviral effect also on combined infection with a virus and a pathogenic bacterium. It has also been observed that a specific *Lactobacillus* strain exhibiting the ability to assimilate wakame has 16S rRNA gene having the same nucleotide sequence as that of the selected antiviral *Lactobacillus* strains and has the action of enhancing the expression of an antiviral factor. It has also been observed that strains of *Lactobacillus plantarum* (also called "*Lactiplantibacillus plantarum*"), a species different from *Lactobacillus salivarius*, which have 16S rRNA gene having an identity of at least 90% with the nucleotide sequence of 16S rRNA gene of *Lactobacillus salivarius* which exhibited an antiviral effect (namely the nucleotide sequence of SEQ ID NO: 1) also have an antiviral effect. The invention has been completed based on the findings.

That is, the invention is as follows.

[1] An antiviral agent containing one, two or more of *Lactobacillus* strains which have 16S rRNA gene having an identity of at least 90% with the nucleotide sequence of SEQ ID NO: 1 and which have an action of enhancing expression of an antiviral factor and/or an action of reducing expression of a downregulator of an antiviral factor.

[2] The antiviral agent described in [1] above, wherein the antiviral factor is one, two or more antiviral factors selected from interferon (IFN)-β, IFN-λ, Mx1 (MX dynamin like GTPase 1), OAS1 (2′-5′-oligoadenylate synthetase 1), RNaseL, PKR (protein kinase R) and RIG-I (retinoic acid inducible gene-I) and that the downregulator of an antiviral factor is one or two downregulators of an antiviral factor selected from A20 and Tollip (Toll-interacting protein).

[3] The antiviral agent described in [1] or [2] above, wherein the *Lactobacillus* strain has an action of enhancing expression of one, two or more receptors selected from TLR (Toll-like receptor) 2, TLR4 and NOD2 (nucleotide binding oligomerization domain-like receptor 2).

[4] The antiviral agent described in any one of [1] to [3] above, wherein the virus is a double-stranded RNA virus.

[5] The antiviral agent described in any of [1] to [4] above, wherein that the *Lactobacillus* strains is one, two or more selected from: a *Lactobacillus salivarius* strain deposited under accession number NITE BP-03218; a *Lactobacillus salivarius* strain deposited under accession number NITE BP-03219; a *Lactobacillus salivarius* strain deposited under accession number NITE BP-03221; a *Lactobacillus plantarum* strain deposited under accession number NITE BP-03474; a *Lactobacillus plantarum* strain deposited under accession number NITE BP-03467; a *Lactobacillus plantarum* strain deposited under accession number NITE BP-03468; a *Lactobacillus plantarum* strain deposited under accession number NITE BP-03466; a *Lactobacillus plantarum* strain deposited under accession number NITE BP-03471; a *Lactobacillus plantarum* strain deposited under accession number NITE BP-03469; a *Lactobacillus plantarum* strain deposited under accession number NITE BP-03470; a *Lactobacillus plantarum* strain deposited under accession number NITE BP-03472; and a *Lactobacillus mucosae* strain deposited under accession number NITE BP-03473.

[6] The antiviral agent described in any one of [1] to [5] above, wherein the *Lactobacillus* strain exhibits an ability to assimilate wakame.

[7] The antiviral agent described in any one of [1] to [6] above, wherein the antiviral agent is livestock feed or a food or a drink.

[8] A *Lactobacillus salivarius* strain deposited under accession number NITE BP-03218; a *Lactobacillus salivarius* strain deposited under accession number NITE BP-03219; a *Lactobacillus salivarius* strain deposited under accession number NITE BP-03221; a *Lactobacillus plantarum* strain deposited under accession number NITE BP-03474; a *Lactobacillus plantarum* strain deposited under accession number NITE BP-03467; a *Lactobacillus plantarum* strain deposited under accession number NITE BP-03468; a *Lactobacillus plantarum* strain deposited under accession number NITE BP-03466; a *Lactobacillus plantarum* strain deposited under accession number NITE BP-03471; a *Lactobacillus plantarum* strain deposited under accession number NITE BP-03469; a *Lactobacillus plantarum* strain deposited under accession number NITE BP-03470; a *Lactobacillus plantarum* strain deposited under accession number NITE BP-03472; or a *Lactobacillus mucosae* strain deposited under accession number NITE BP-03473.

Other embodiments of the invention include:

a method for preventing and/or treating viral infection, including a step of administering one, two or more of *Lactobacillus* strains which have 16S rRNA gene (16S rDNA) having an identity of at least 90% with the nucleotide sequence of SEQ ID NO: 1 and which have the action of enhancing the expression of an antiviral factor and/or the action of reducing the expression of a downregulator of an antiviral factor (sometimes called "the *Lactobacillus* strains of this case" below) to a subject (patient) in need of prevention and/or treatment of viral infection (preferably viral infection in combined infection with a virus and a pathogenic bacterium);

one, two or more of the *Lactobacillus* strains of this case for use as an antiviral agent;

one, two or more of the *Lactobacillus* strains of this case for use in antiviral application;

one, two or more of the *Lactobacillus* strains of this case for use in the prevention and/or the treatment of viral infection;

use of one, two or more of the *Lactobacillus* strains of this case for the manufacture of an antiviral agent; and use of one, two or more of the *Lactobacillus* strains of this case for the manufacture of an agent for preventing and/or treating viral infection.

Advantageous Effects of Invention

The *Lactobacillus* strains of this case have the action of enhancing the expression of an antiviral factor or the action of reducing the expression of a downregulator of an antiviral factor and effectively exhibit an antiviral effect also on combined infection with a virus and a pathogenic bacterium. Moreover, the *Lactobacillus* strains of this case are bacterial strains which live in symbiosis in the body (especially in the intestinal tract) of the host mammal (namely probiotics) and thus can effectively prevent/improve (treat) viral infection (preferably viral infection in combined infection with a virus and a pathogenic bacterium) in a human or a nonhuman mammal (especially livestock) with few side effects, unlike vaccines or antibiotics. Furthermore, when a *Lactobacillus* strain of this case has the ability to assimilate wakame, an immunosymbiotic of the *Lactobacillus* strain of this case having the ability to assimilate wakame (preferably an antiviral immunobiotic) and wakame (a prebiotic) promotes the proliferation of the bacterial strain, and thus the antiviral effect of the *Lactobacillus* strain of this case can be exhibited more effectively.

BRIEF DESCRIPTION OF DRAWINGS

FIG. 1—A figure showing the results of analysis of the expression levels of two antiviral factors (IFN-β [FIG. 1A] and Mx1 [FIG. 1B]) in a porcine intestinal epitheliocyte line (a PIE cell line) stimulated with poly I:C. The time after the stimulation with poly I:C is shown. In the figure, "*", "" and "*" indicate statistically significant differences ($p<0.05$, $p<0.01$ and $p<0.001$) from the results at 0 hour.

FIG. 7—FIGS. 7A to C are figures showing the results of analysis of the expression levels of A20 (FIG. 7A) and the expression levels of Tollip (FIGS. 7B and C) in the PIE cell line stimulated with strain #35 of this case ("#35" in the figure) or strain #58 of this case ("#58" in the figure) before stimulation with poly I:C for six hours, three hours and 12 hours. In the figure, "" and "*" indicate statistically significant differences ($p<0.01$ and $p<0.001$) from the results of the case with stimulation only with poly I:C ("POLY(I:C)+" in the figure).

Figures 8A, 8B:
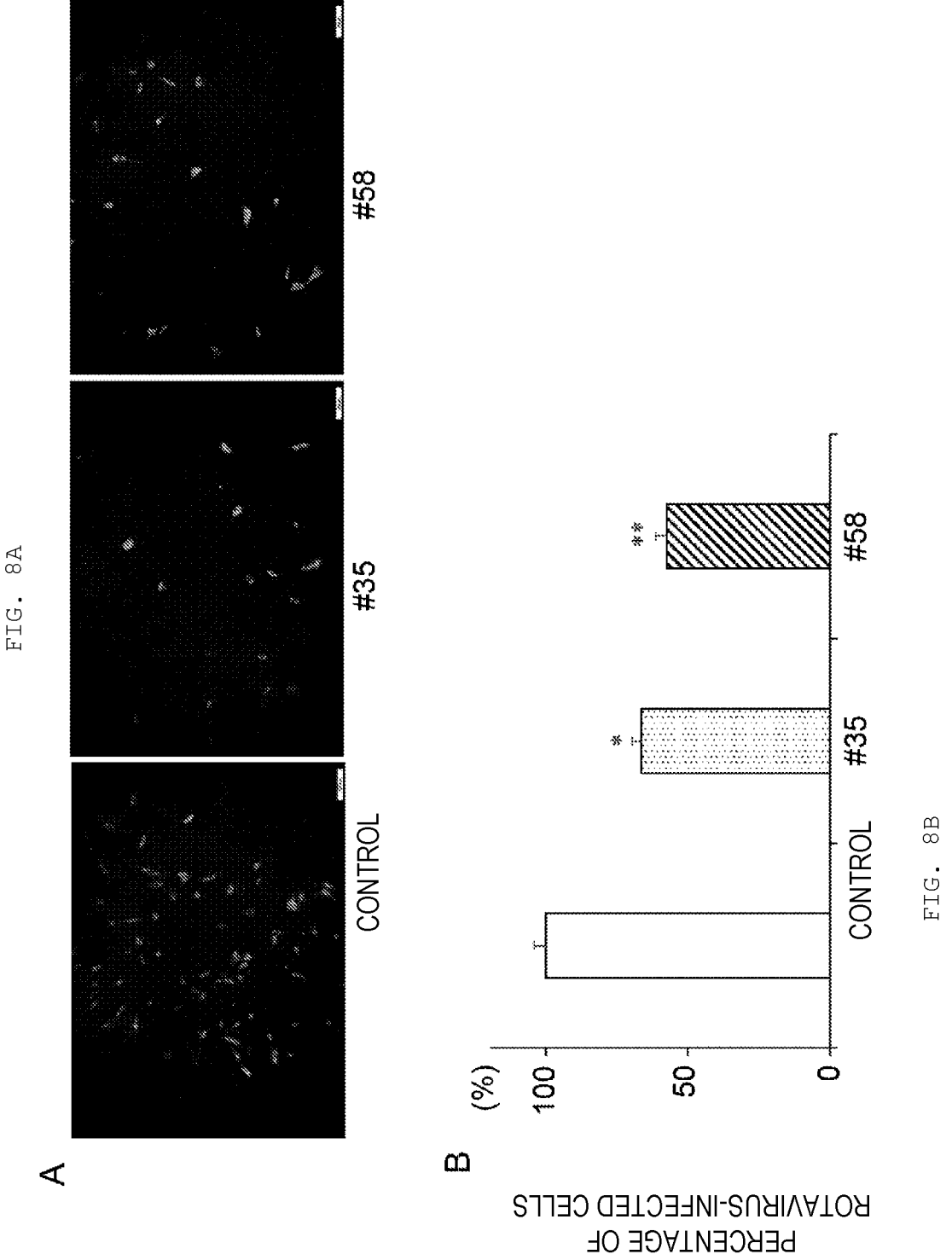

FIG. 8—FIG. 8A shows fluorescence images analyzing the PIE cell line which was stimulated with strain #35 of this case ("#35" in the figure) or strain #58 of this case ("#58" in the figure) or was not stimulated with the strains ("CONTROL" in the figure) before incubation in an active rotavirus solution by indirect fluorescent antibody assay using an anti-rotavirus antibody. FIG. 8B is a figure showing the results of analysis of the percentages of rotavirus-infected cells based on the results in FIG. 8A. The percentages of rotavirus-infected cells are values relative to that of the control set to 100. In the figure, "*" and "**" indicate statistically significant differences ($p<0.05$ and $p<0.01$) from the control value.

Figures 9A, 9B, 9C, 9D, 10A, 10B:
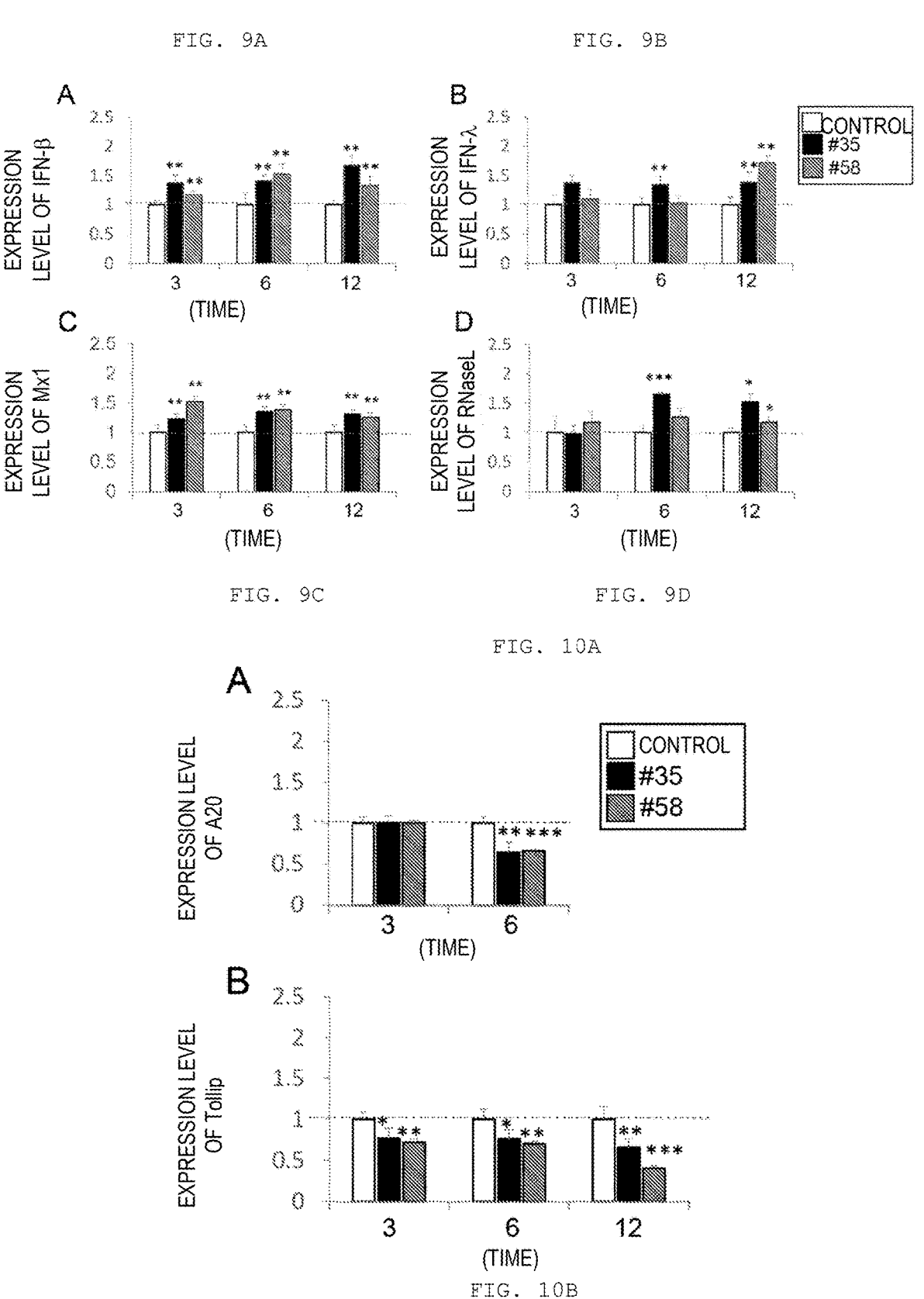

FIG. 9—A figure showing the results of analysis of the expression levels of four antiviral factors (IFN-β [FIG. 9A], IFN-λ [FIG. 9B], Mx1 [FIG. 9C] and RNaseL [FIG. 9D]) in the PIE cell line which was stimulated with strain #35 of this case ("#35" in the figure) or strain #58 of this case ("#58" in the figure) or was not stimulated with the strains ("CONTROL" in the figure) before incubation in an active rotavirus solution for three hours, six hours or 12 hours. The expression levels of the antiviral factors are values relative to those of the controls set to 1. In the figure, "*", "" and "*" indicate statistically significant differences ($p<0.05$, $p<0.01$ and $p<0.001$) from the control values.

FIG. 10—FIG. 10A is a figure showing the results of analysis of the expression levels of A20 in the PIE cell line which was stimulated with strain #35 of this case ("#35" in the figure) or strain #58 of this case ("#58" in the figure) or was not stimulated with the strains ("CONTROL" in the figure) before incubation in an active rotavirus solution for three hours or six hours. FIG. 10B is a figure showing the results of analysis of the expression levels of Tollip in the PIE cell line which was stimulated with strain #35 of this case ("#35" in the figure) or strain #58 of this case ("#58" in the figure) or was not stimulated with the strains ("CONTROL" in the figure) before incubation in the active rotavirus solution for three hours, six hours or 12 hours. The expression levels of A20 and the expression levels of Tollip are values relative to those of the controls set to 1. In the figure, "*", "" and "*" indicate statistically significant differences ($p<0.05$, $p<0.01$ and $p<0.001$) from the control values.

FIG. 11—FIG. 11A is a figure showing the results of analysis of the percentages of rotavirus-infected cells in the PIE cell line which was incubated in an active rotavirus solution alone ("VIRUS" in the figure) or incubated in the active rotavirus solution and an ETEC-containing solution ("VIRUS+ETEC" in the figure). The percentage of rotavirus-infected cells is a value relative to that of "VIRUS+ETEC" set to 100. FIG. 11B is a figure showing the results of analysis of the percentages of rotavirus-infected cells in the PIE cell line which was stimulated with strain #35 of this case ("#35" in the figure) or strain #58 of this case ("#58" in the figure) or was not stimulated with the strains ("CONTROL" in the figure) before incubation in the active rotavirus solution and the ETEC-containing solution. The percentages of rotavirus-infected cells are values relative to that of the control set to 100. In the figure, "***" indicates a statistically significant difference ($p<0.001$).

FIG. 12—A figure showing the results of analysis of the expression levels of three antiviral factors (IFN-β [FIG. 12A], IFN-λ [FIG. 12B] and Mx1 [FIG. 12C]) in the PIE cell line which was stimulated with strain #35 of this case ("#35" in the figure) or strain #58 of this case ("#58" in the figure) or was not stimulated with the strains ("CONTROL" in the figure) before incubation in an active rotavirus solution and an ETEC-containing solution for three hours, six hours or 12 hours. The expression levels of the antiviral factors are values relative to those of the controls set to 1. In the figure, "*", "" and "*" indicate statistically significant differences ($p<0.05$, $p<0.01$ and $p<0.001$) from the control values.

FIG. 13—A figure showing the results of analysis of the expression levels of three antiviral factors (RNaseL [FIG. 13A], PKR [FIG. 13B] and RIG-1 [FIG. 13C]) in the PIE cell line which was stimulated with strain #35 of this case ("#35" in the figure) or strain #58 of this case ("#58" in the figure) or was not stimulated with the strains ("CONTROL" in the figure) before incubation in an active rotavirus solution and an ETEC-containing solution for three hours, six hours or 12 hours. The expression levels of the antiviral factors are values relative to those of the controls set to 1. In the figure, "*", "" and "*" indicate statistically significant differences ($p<0.05$, $p<0.01$ and $p<0.001$) from the control values.

Figure 14A:
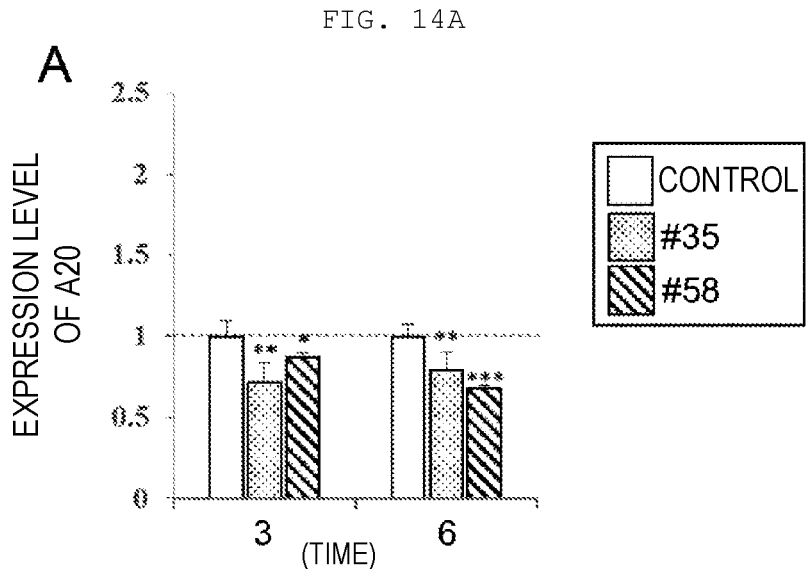
Figure 14B:
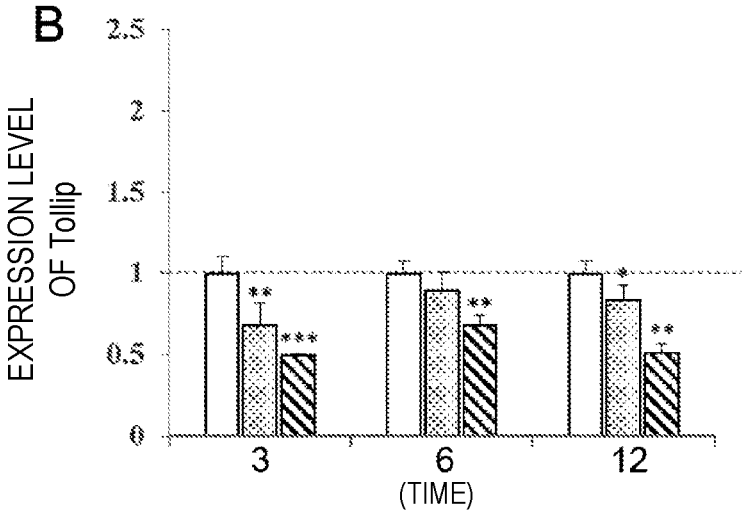

FIG. 14—FIG. 14A is a figure showing the results of analysis of the expression levels of A20 in the PIE cell line which was stimulated with strain #35 of this case ("#35" in the figure) or strain #58 of this case ("#58" in the figure) or was not stimulated with the strains ("CONTROL" in the figure) before incubation in an active rotavirus solution and an ETEC-containing solution for three hours or six hours. FIG. 14B is a figure showing the results of analysis of the expression levels of Tollip in the PIE cell line which was stimulated with strain #35 of this case ("#35" in the figure) or strain #58 of this case ("#58" in the figure) or was not stimulated with the strains ("CONTROL" in the figure) before incubation in the active rotavirus solution and the ETEC-containing solution for three hours, six hours or 12 hours. The expression levels of A20 and the expression levels of Tollip are values relative to those of the controls set to 1. In the figure, "*", "" and "*" indicate statistically significant differences ($p<0.05$, $p<0.01$ and $p<0.001$) from the control values.

Figures 15A, 15B:
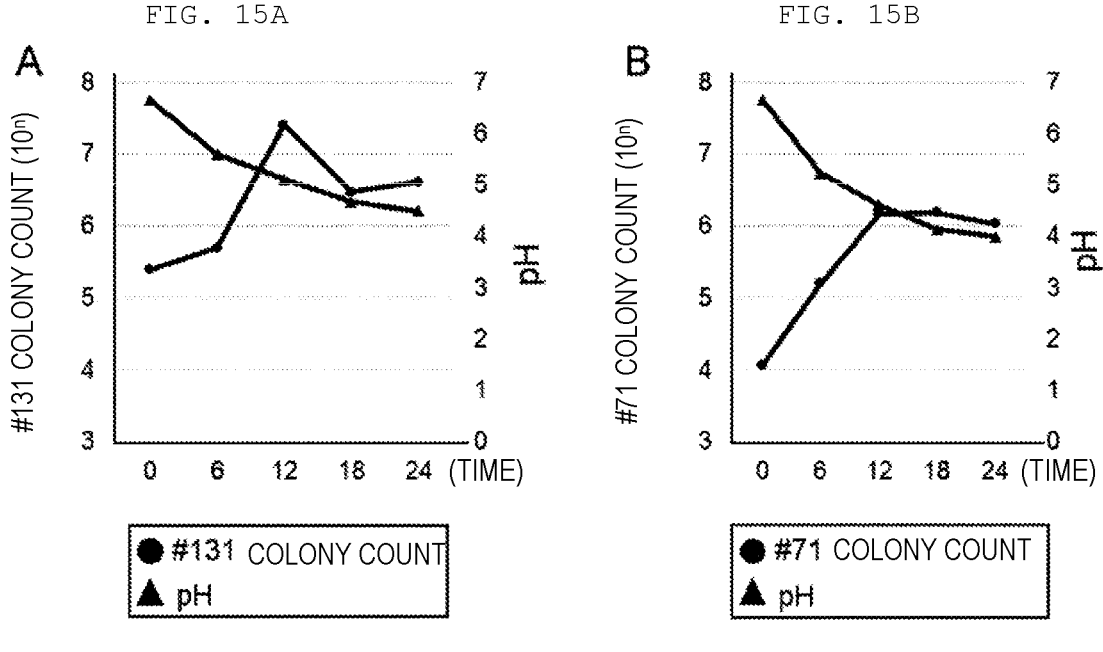

FIG. 15—A figure showing the results of measurement of the colony counts and the medium pH of strain #131 of this case ("#131" in the figure) or strain #71 of this case ("#71" in the figure) which was cultured on a wakame component-adjusted agar plate.

Figure 16:
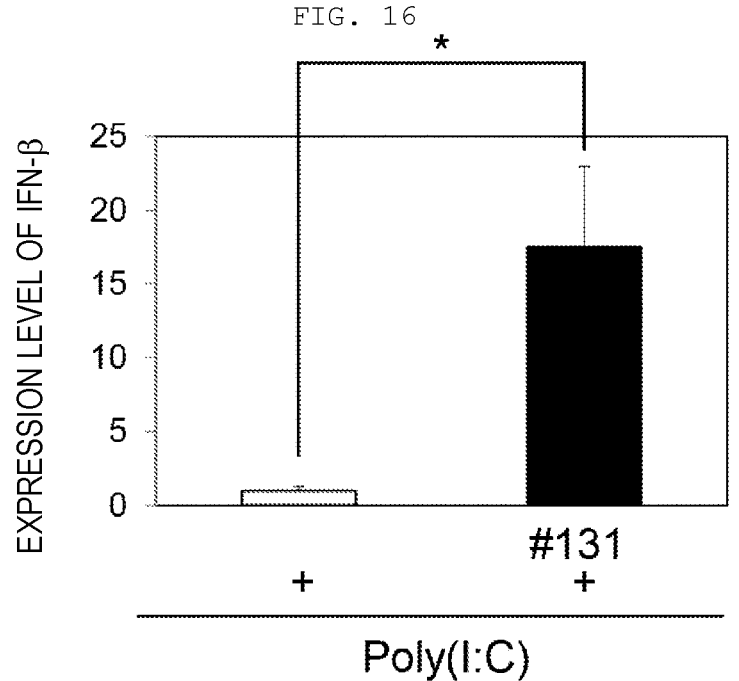

FIG. 16—A figure showing the results of analysis of the expression level of an antiviral factor (IFN-β) in the PIE cell line stimulated with strain #131 of this case before stimulation with poly I:C (right column). In the figure, "*" indicates a statistically significant difference ($p<0.05$) from the results of the case with stimulation only with poly I:C (left column).

Figure 17:
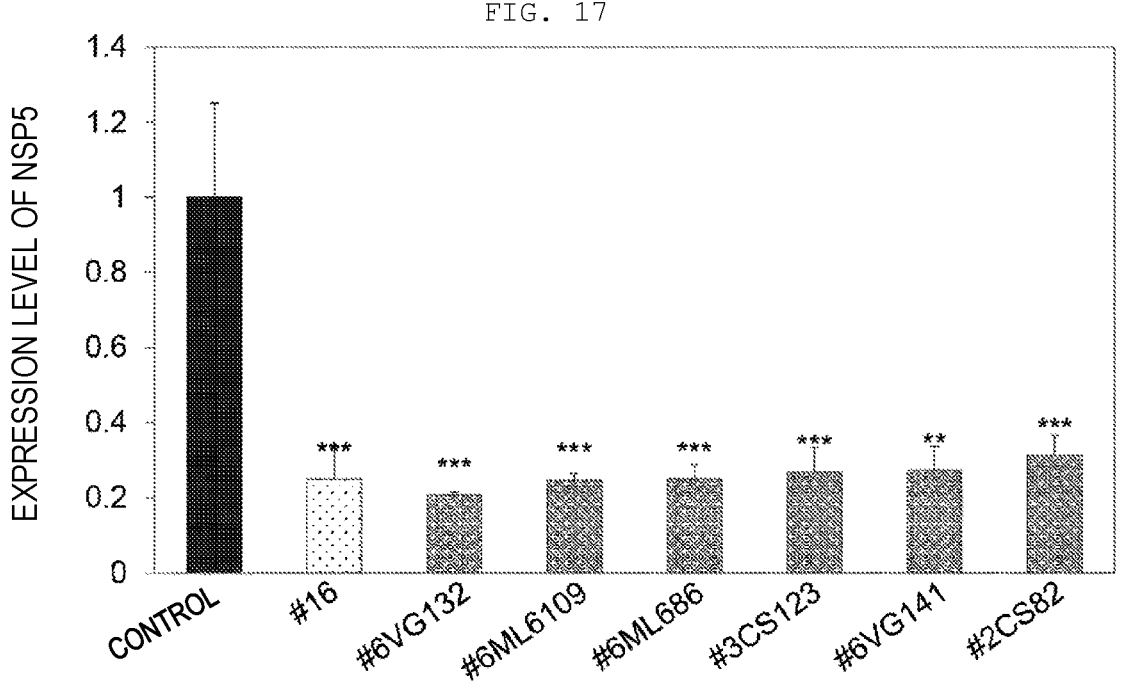

FIG. 17—A figure showing the results of analysis of the expression levels of NSP5 in a PIE1-3 cell line which was stimulated with seven Lactobacillus strains of this case (strain #16 of this case ["#16" in the figure], strain #6VG132 of this case ["#6VG132" in the figure], strain #6ML6109 of this case ["#6ML6109" in the figure], strain #6ML686 of this case ["#6ML686" in the figure], strain #3CS123 of this case ["#3CS123" in the figure], strain #6VG141 of this case ["#6VG141" in the figure] and strain #2CS82 of this case ["#2CS82" in the figure]) or was not stimulated with the strains ("CONTROL" in the figure) before incubation in an active rotavirus solution. In the figure, "" and "*" indicate statistically significant differences ($p<0.01$ and $p<0.001$) from the control value.

Figure 18:
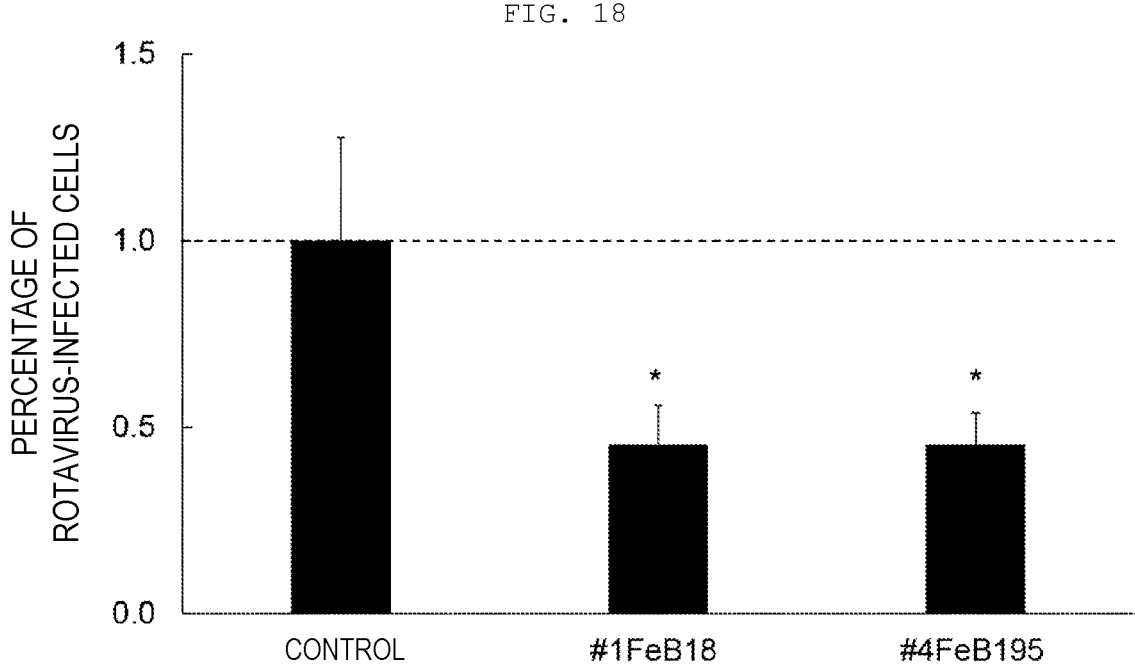

FIG. 18—A figure showing the results of analysis of the percentages of rotavirus-infected cells in a PIE1-3 cell line which was stimulated with two Lactobacillus strains of this case (strain #1FeB18 of this case ["#1FeB18" in the figure] and strain #4FeB195 of this case ["#4FeB195" in the figure]) or was not stimulated with the strains ("CONTROL" in the figure) before incubation in an active rotavirus solution. The percentages of rotavirus-infected cells are values relative to that of the control set to 1. In the figure, "*" indicates a statistically significant difference ($p<0.05$) from the control value.

DESCRIPTION OF EMBODIMENTS

The antiviral agent of the invention is an agent containing one, two or more of the Lactobacillus strains of this case (namely, Lactobacillus strains which have 16S rRNA gene having an identity of at least 90% with the nucleotide sequence of SEQ ID NO: 1 and which have the action of enhancing the expression of an antiviral factor and/or the action of reducing the expression of a downregulator of an antiviral factor) which is specified for "antiviral" application (sometimes called "the antiviral agent of this case" below). Here, the 16S rRNA gene is generally contained in the genome DNA of the Lactobacillus strains of this case.

Regarding the antiviral agent of this case, the Lactobacillus strains of this case, which are antiviral probiotics, may be used alone as livestock feed, a food or a drink or a pharmaceutical product (formulation) or may be used in the form of a composition further containing an additive (a livestock feed composition, a food or drink composition or a pharmaceutical composition). Examples of the food or the drink include health foods (functional foods, nutritional supplements, dietary supplements, enriched foods, balanced foods, supplements and the like) and food with health claims (foods for specified health uses, foods with nutrient function claims, foods with function claims and the like). The antiviral agent of this case is preferably livestock feed or a food or a drink.

In the present specification, the "antiviral" means to prevent and/or to improve (treat) of viral infection through the action of suppressing the multiplication of the virus, inactivating the virus or reducing the sensitivity to the virus or another action.

The antiviral factor may be a factor which causes an antiviral action in mammalian cells (such as polypeptides, proteins [specifically, cytokines and antibodies], polynucleotides, saccharides and lipids), and examples thereof include interferon (IFN)-α, IFN-β, IFN-λ, Mx1 (MX dynamin like GTPase 1), OAS1 (2'-5'-oligoadenylate synthetase 1), RNaseL, PKR (protein kinase R), RIG-I (retinoic acid inducible gene-I), ISG15 (IFN stimulated gene 15 kDa), MDA5 (melanoma differentiation-associated gene 5), IPS-1 (interferon-β promoter stimulator-1) and the like. Because the effects have been demonstrated in the Examples described below, one, two or more antiviral factors selected from IFN-β, IFN-λ, Mx1, OAS1, RNaseL, PKR and RIG-I are suitable examples.

The "downregulator of an antiviral factor" may be a factor which causes reduction in the expression of an antiviral factor (such as polypeptides, proteins, polynucleotides, saccharides and lipids), and examples thereof include A20 (also called TNFAIP3 [Tumor Necrosis Factor Alpha-Induced Protein 3]), Tollip (Toll-interacting protein), RNF125 (Ring Finger Protein 125), DUBA (deubiquitinase A), CYLD (CYLD lysine 63 deubiquitinase) and the like. Because the effects have been demonstrated in the Examples described below, one or two downregulators of an antiviral factor selected from A20 and Tollip are suitable examples.

The *Lactobacillus* strains of this case can be characterized by the action of enhancing the expression of one, two or more receptors selected from TLR (Toll-like receptor) 2, TLR4 and NOD2 (nucleotide binding oligomerization domain-like receptor 2) (sometimes called "antiviral factor receptors" below).

In the present specification, the expression of the antiviral factor, the downregulator of an antiviral factor and the antiviral factor receptor (sometimes together called "the antiviral factor or the like" below) means the expression of the antiviral factor or the like itself and/or the expression of the transcription product (specifically mRNA) of the gene encoding the antiviral factor or the like (namely the gene of the antiviral factor or the like). The expression level of the antiviral factor or the like can be detected using a method such as the western blot, indirect fluorescent antibody technique, flow cytometry, ELISA, EIA and RIA. Regarding the expression level of the transcription product of the gene of the antiviral factor or the like, mRNA of the gene of the antiviral factor or the like can be directly detected, or cDNA synthesized from the mRNA of the gene of the antiviral factor or the like as a template can be indirectly detected. Examples of the method for detecting the mRNA of the gene of the antiviral factor or the like include methods such as (Reverse Transcription)-PCR, the northern blot, microarrays and ISH. Examples of the method for detecting the cDNA synthesized from the mRNA of the gene of the antiviral factor or the like as a template include LAMP, PCR (for example, real-time PCR [intercalation, 5'-nuclease method, cycling probe technology or the like] or ddPCR), LCR, sequencing using a next-generation sequencer, Southern hybridization using a probe for detecting the cDNA of this case or the like, microarrays, ISH and the like.

In the present specification, "enhancement of the expression of an antiviral factor", "reduction of the expression of a downregulator of an antiviral factor" and "enhancement of the expression of an antiviral factor receptor" mean "an increase in the expression level of the antiviral factor", "reduction in the expression level of the downregulator of an antiviral factor" and "an increase in the expression level of the antiviral factor receptor", respectively, when a mammalian cell line is cultured in the presence of a *Lactobacillus* strain of this case compared to the control for comparison in which the mammalian cell line is cultured in the absence of the *Lactobacillus* strain of this case. The mammalian cell line may be stimulated with a virus as the subject of the antiviral agent of this case, a substance inducing pseudovirus infection (for example, polyinosinic-polycytidylic acid [poly I:C]) and/or a pathogenic bacterium before or after culturing in the presence or absence of the *Lactobacillus* strain of this case. When observing whether the expression level of the antiviral factor or the like has increased or decreased, any threshold value (cut-off value) may be set. Examples of the threshold value include the average, the average+the standard deviation (SD), the average+2SD, the average+3SD, the median, the interquartile range and the like of the expression levels of the antiviral factor or the like in the control for comparison. The threshold value can also be calculated using the ROC (Receiver Operating Characteristic) curve using statistical analysis software based on the expression level data obtained by culturing the mammalian cell line in the presence of the *Lactobacillus* strain of this case and the expression level data obtained by culturing the mammalian cell line in the absence of the *Lactobacillus* strain of this case in such a manner that the sensitivity (the percentage that the mammalian cell line cultured in the presence of the *Lactobacillus* strain of this case can be correctly determined to be positive) and the specificity (the percentage that the mammalian cell line cultured in the absence of the *Lactobacillus* strain of this case can be correctly determined to be negative) become high.

Examples of the mammalian cell line include a human intestinal epitheliocyte (Caco-2) line, a porcine intestinal epitheliocyte line (a PIE cell line) and a bovine intestinal epitheliocyte line (a BIE cell line).

The virus as the subject of the antiviral agent of this case is not particularly restricted, and examples thereof include DNA viruses (double-stranded DNA viruses, single-stranded DNA viruses and the like), RNA viruses (double-stranded RNA viruses, single-stranded positive-strand RNA viruses, single-stranded negative-strand RNA viruses and the like) and the like. Because the effects on a double-stranded RNA model virus have been demonstrated in the Examples described below, a double-stranded RNA virus is preferable. More specific examples of the subject virus include influenza viruses (single-stranded negative-strand RNA viruses), noroviruses (single-stranded positive-strand RNA viruses), rotaviruses (double-stranded RNA viruses), rubella virus (single-stranded positive-strand RNA virus), measles virus (single-stranded positive-strand RNA virus), RS virus (single-stranded negative-strand RNA virus), herpesviruses (double-stranded DNA viruses), hepatitis A virus (single-stranded positive-strand RNA virus), hepatitis B virus (double-stranded DNA virus), hepatitis C virus (single-stranded positive-strand RNA virus), hepatitis E virus (single-stranded positive-strand RNA virus), adenoviruses (double-stranded DNA viruses), foot-and-mouth disease virus (single-stranded positive-strand RNA virus), rabies virus (single-stranded negative-strand RNA virus), human immunodeficiency viruses (single-stranded positive-strand RNA viruses), coronaviruses (single-stranded positive-strand RNA viruses) and the like. Because the effects have been demonstrated in the Examples described below, a rotavirus is a suitable example. Influenza viruses include type A virus, type B virus, type C virus, avian influenza viruses and subtypes thereof, and coronaviruses include, in addition to general coronaviruses which cause common cold, new coronaviruses (for example, severe acute respiratory syndrome coronaviruses [SARS and SARS-CoV-2], Middle East respiratory syndrome coronavirus [MERS] and COVID-19).

The subject to which the antiviral agent of this case is applied is a mammal in need of prevention and/or improvement (treatment) of viral infection, and a suitable example thereof is a mammal in need of prevention and/or improvement (treatment) of viral infection in combined infection with a virus and a pathogenic bacterium because it has been demonstrated in the Examples described below that an antiviral effect is effectively exhibited also on combined infection with a virus and a pathogenic bacterium.

In the present specification, examples of the pathogenic bacterium include *Mycoplasma* species, diarrheagenic *Escherichia coli* (for example, enteropathogenic *Escherichia coli* [EPEC], enteroinvasive *Escherichia coli* [EIEC], enterotoxigenic *Escherichia coli* [ETEC], enteroaggregative *Escherichia coli* [EAggEC] and enterohemorrhagic *Escherichia coli* [EHEC]), hemolytic streptococci and the like.

In the present specification, the mammal may be a human, a nonhuman mammal (for example, a monkey, a mouse, a rat, a dog, a cat and a livestock animal [for example, a rabbit, a pig, a horse, a cow, a sheep, a goat and a deer]) or the like, and a human and a livestock animal are suitable examples.

The *Lactobacillus* strains of this case may be bacterial strains in the living state or bacterial strains in the dead state as long as the *Lactobacillus* strains have 16S rRNA gene having an identity of at least 90% with the nucleotide sequence of SEQ ID NO: 1 and have the action of enhancing the expression of an antiviral factor and/or the action of reducing the expression of a downregulator of an antiviral factor. The *Lactobacillus* strains of this case include the *Lactobacillus salivarius* strains or the *Lactobacillus plantarum* strains which have been demonstrated to exhibit an effect in the Examples described below and *Lactobacillus* strains which are of different species from the *Lactobacillus salivarius* strains or the *Lactobacillus plantarum* strains (for example, *Lactobacillus hayakitensis, Lactobacillus agilis, Lactobacillus aviarius* subsp. *araffinosus* and *Lactobacillus aviarius* subsp. *aviarius*) and which have 16S rRNA gene having an identity of at least 90% with the nucleotide sequence of SEQ ID NO: 1 and have the action of enhancing the expression of an antiviral factor and/or the action of reducing the expression of a downregulator of an antiviral factor. The *Lactobacillus* strains of this case specifically include: a *Lactobacillus salivarius* strain deposited under international deposit accession number NITE BP-03218 (strain #35 of this case), a *Lactobacillus salivarius* strain deposited under international deposit accession number NITE BP-03219 (strain #58 of this case), a *Lactobacillus salivarius* strain deposited under international deposit accession number NITE BP-03221 (strain #131 of this case) and a *Lactobacillus salivarius* strain deposited under international deposit accession number NITE BP-03220 (strain #71 of this case); and a *Lactobacillus plantarum* strain deposited under international deposit accession number NITE BP-03474 (strain #16 of this case), a *Lactobacillus plantarum* strain deposited under international deposit accession number NITE BP-03467 (strain #6VG132 of this case), a *Lactobacillus plantarum* strain deposited under international deposit accession number NITE BP-03468 (strain #6ML6109 of this case), a *Lactobacillus plantarum* strain deposited under international deposit accession number NITE BP-03466 (strain #6ML686 of this case), a *Lactobacillus plantarum* strain deposited under international deposit accession number NITE BP-03471 (strain #3CS123 of this case), a *Lactobacillus plantarum* strain deposited under international deposit accession number NITE BP-03469 (strain #6VG141 of this case), a *Lactobacillus plantarum* strain deposited under international deposit accession number NITE BP-03470 (strain #2CS82 of this case), a *Lactobacillus plantarum* strain deposited under international deposit accession number NITE BP-03472 (strain #1FeB18 of this case) and a *Lactobacillus mucosae* strain deposited under international deposit accession number NITE BP-03473 (strain #4FeB195 of this case). Because the antiviral effect has been demonstrated in the Examples described below, one, two or more selected from the *Lactobacillus salivarius* strain deposited under international deposit accession number NITE BP-03218 (strain #35 of this case), the *Lactobacillus salivarius* strain deposited under international deposit accession number NITE BP-03219 (strain #58 of this case), the *Lactobacillus salivarius* strain deposited under international deposit accession number NITE BP-03221 (strain #131 of this case), the *Lactobacillus plantarum* strain deposited under international deposit accession number NITE BP-03474 (strain #16 of this case), the *Lactobacillus plantarum* strain deposited under international deposit accession number NITE BP-03467 (strain #6VG132 of this case), the *Lactobacillus plantarum* strain deposited under international deposit accession number NITE BP-03468 (strain #6ML6109 of this case), the *Lactobacillus plantarum* strain deposited under international deposit accession number NITE BP-03466 (strain #6ML686 of this case), the *Lactobacillus plantarum* strain deposited under international deposit accession number NITE BP-03471 (strain #3CS123 of this case), the *Lactobacillus plantarum* strain deposited under international deposit accession number NITE BP-03469 (strain #6VG141 of this case), the *Lactobacillus plantarum* strain deposited under international deposit accession number NITE BP-03470 (strain #2CS82 of this case), the *Lactobacillus plantarum* strain deposited under international deposit accession number NITE BP-03472 (strain #1FeB18 of this case) and the *Lactobacillus mucosae* strain deposited under international deposit accession number NITE BP-03473 (strain #4FeB195 of this case) are suitable examples.

In the invention, the "identity of at least 90% with the nucleotide sequence of SEQ ID NO: 1" means that one or several nucleotides in the nucleotide sequence of SEQ ID NO: 1 are substituted, deleted, inserted, added or inverted and that the 90% or more of the whose sequence is identical with the nucleotide sequence of SEQ ID NO: 1. Here, the "nucleotide sequence in which one or several nucleotides are substituted, deleted, inserted, added or inverted" means a nucleotide sequence in which for example 1 to 149, preferably 1 to 100, more preferably 1 to 75, further preferably 1 to 50, more preferably 1 to 40, further preferably 1 to 30, more preferably 1 to 15 nucleotides are substituted, deleted, inserted, added or inverted.

In the invention, the "identity of at least 90%" is an identity of preferably 91% or more, more preferably 92% or more, further preferably 93% or more, still further preferably 94% or more, particularly preferably 95% or more, particularly more preferably 96% or more, particularly further preferably 97% or more, particularly still further preferably 98% or more, most preferably 99% or more (about 100%). The nucleotide sequence identity can be determined using a program called BLASTN (Altschul S F, et al: J Mol Biol 215: 403, 1990) based on a program called BLASTX or BLASTP (Altschul S F, et al: J Mol Biol 215: 403, 1990) based on algorism BLAST of Karlin and Altschul (Proc. Natl. Acad. Sci. USA 87:2264-2268, 1990, Proc Natl Acad Sci USA 90: 5873, 1993). When nucleotide sequences are analyzed using BLASTN, the parameters are, for example, score=100 and word length=12.

The *Lactobacillus* strains of this case also include those further having the ability to assimilate wakame. Here, "the ability to assimilate wakame" means the ability to synthesize substances necessary for the *Lactobacillus* spp. such as proteins, nucleic acids, saccharides and lipids from wakame as a carbon source or a nitrogen source.

The antiviral agents of this case are roughly classified into liquid type and non-liquid type. The antiviral agent of this case of liquid type can be produced by purifying a culture solution of a *Lactobacillus* strain of this case, adding appropriate physiological saline, fluid replacement or a pharmaceutical additive thereto according to the need and packing in an ampule, a vial or the like. The antiviral agent of this case in non-liquid type can be produced by adding an appropriate cryoprotectant (for example, glycerol, dimethyl sulfoxide [DMSO], trehalose or dextran) to the antiviral agent of this case of liquid type, packing in an ampule, a vial or the like and then freezing or lyophilizing.

As the application (administration) method of the antiviral agent of this case, both an oral application method (oral administration) and a parenteral application method (parenteral administration) may be used, and examples of the parenteral application method (parenteral administration) include intravenous administration and topical administration.

In the present specification, examples of the additive include pharmaceutically acceptable general ingredients such as a carrier, a binder, a stabilizer, an excipient, a diluent, a pH buffer, a disintegrant, an isotonic agent, an additive, a coating agent, a solubilizer, a lubricant, a sliding agent, a solubilizing agent, a lubricator, an aroma, a sweetener, a solvent, a gelling agent and a nutrient. Specific examples of the ingredients include water, a wakame component, physiological saline, animal fat and oil, vegetable oil, lactose, starch, gelatin, crystalline cellulose, gum, talc, magnesium stearate, hydroxypropyl cellulose, polyalkylene glycol, polyvinyl alcohol and glycerin. When the *Lactobacillus* strains of this case have the ability to assimilate wakame, those containing a wakame component (a prebiotic), which is the nutrient source of the *Lactobacillus* strains of this case, as an additive and containing an immunosymbiotic of the *Lactobacillus* strains of this case (preferably an antiviral immunobiotic) and a prebiotic are suitable examples of the antiviral agent of this case. The wakame component may be wakame powder obtained by crushing dried wakame or a wakame component extract solution obtained by further extracting from the wakame powder with water or the like.

The applied amount (dosage) of the *Lactobacillus* strains of this case contained in the antiviral agent of this case cannot be specified generally because the amount varies with the gender, the age, the body weight, the condition and the like of the subject of intake (mammal), but the amount is, for example, $10^4$ to $10^{12}$ cfu (Colony Forming Unit), preferably $10^6$ to $10^{10}$ cfu per day per 1 kg body weight. The amount may be taken at one time or taken in several divided portions. When the antiviral agent of this case is a livestock feed composition, the amount of the *Lactobacillus* strains of this case contained in the livestock feed composition is, for example, $10^4$ to $10^{12}$ cfu/g, preferably $10^6$ to $10^{10}$ cfu per 1 g of the livestock feed composition.

The invention is explained more specifically below with Examples, but the technical scope of the invention is not limited to the examples. In this regard, special grade or 1st grade reagents manufactured by Wako Pure Chemical Industries, Ltd. were used as the reagents unless otherwise specified, and MILLI-Q® grade water was used as water.

EXAMPLES

Example 1. Search of Antiviral Factors

Factors as indicators for evaluating the antiviral activity of a probiotic were searched.
1-1 Materials and Methods
[Tested Cells]
As the PIE cell line, cells cloned from the small intestine of a newborn 3-way cross pig (LWD; Landrace×Large White×Duroc) were used.
[Cell Culture]
The PIE cell line was cultured using a 250-mL flask coated with type I collagen (manufactured by Sumitomo Bakelite Co., Ltd.) in 10% FCS (fetal calf serum)- and 1% streptomycin/penicillin-containing DMEM liquid medium (containing high glucose, L-glutamine and sodium pyruvate; manufactured by GIBCO) (simply called "DMEM liquid medium" below). When the cells became confluent, the cells were washed twice with PBS and incubated at 37° C. for five minutes in an epithelium buffer (a PBS solution containing 0.1M disodium hydrogen phosphate dodecahydrate, 0.45M sucrose, 0.36% EDTA-4Na and 0.1% BSA). Then, the epithelium buffer was removed, and the cells were incubated at 37° C. for five minutes in PBS containing 0.25% trypsin and 0.02% EDTA. After adding DMEM liquid medium and collecting detached cells, centrifugation (12000 rpm×five minutes) was conducted, and the culture supernatant was removed. Fresh DMEM liquid medium was added, and the cells were collected. After counting the cells, the cells were seeded at $1×10^6$ cells per flask. After culturing for 24 hours, the culture supernatant was removed by suction with an aspirator, and fresh DMEM liquid medium was added, followed by culturing. Each generation of the cells was stored at −80° C. using Cellbanker (registered trademark) (manufactured by Nippon Zenyaku Kogyo Co., Ltd.). The cells were cultured under the conditions of 5% $CO_2$/20% $O_2$ at 37° C.

[Expression Analysis of Cytokine-Related Factors in Poly I:C-Stimulated PIE Cell Line]

The PIE cell line was stimulated with poly I:C, which is a double-stranded RNA virus model inducing pseudo-virus infection, and the expression of cytokine-related factors was analyzed. Specifically, the analysis was conducted according to the following procedures [1] to [5].

[1] The PIE cell line was seeded in 12-well plates coated with type I collagen (manufactured by Sumitomo Bakelite Co., Ltd.) at $3×10^4$ cells/well and cultured in DMEM liquid medium for five days.

[2] The medium was replaced with DMEM liquid medium containing 50 ng/ml poly I:C (catalog number P9582, manufactured by SIGMA), and the cells were cultured for 0, 3, 6 and 12 hours and thus stimulated with poly I:C. As a control which was not stimulated with poly I:C, the PIE cell line was cultured similarly in poly I:C-free DMEM liquid medium.

[3] After removing the medium, the cells were washed once with PBS, and the total RNA of the cells was obtained according to a standard method using a cell-dissolving solution (TRIzol reagent [manufactured by Invitrogen]). The concentration and the purity of the RNA were measured with NANODROP® ND-1000 spectrophotometer (manufactured by Thermo Fisher Scientific).

[4] cDNA was synthesized from the obtained total RNA using PRIMESCRIPT™ RT reagent Kit with gDNA Eraser (Perfect Real Time) (manufactured by Takara) according to the protocols attached to the product.

[5] To analyze the mRNA expression levels of the genes of 24 cytokine-related factors (IFN-β, IFN-λ, Mx1, OAS1, RNaseL, PKR, RIG-I, TLR2, TLR3, TLR4, NOD1, NOD2, MCP-1 [also called CCL2], IL-6, IL-8 [also called CXCL8], IL-12, IL-18, TNFα, A20, BCL-3, Tollip, IRAK-M, MKP-1 and SIGIRR) and β-actin, quantitative PCR analysis was conducted using the synthesized cDNA as a template, using the primer sets shown in Table 1 below (the sense primers and the antisense primers), PLATINUM™ SYBR™ Green qPCR Super Mix-UDG with ROX (manufactured by Invitrogen) and ABI PRISM 7300 real-time PCR system (manufactured by Applied Biosystem) according to the protocols attached to the product. The expression levels of the cytokine-related factors with the poly I:C-stimulation were calculated based on the equation ([the mRNA expression level of the cytokine-related factor gene/the mRNA expression level of β-actin gene] with the poly I:C-stimulation/[the mRNA expression level of the cytokine-related factor gene/ the mRNA expression level of β-actin gene] without the poly I:C-stimulation).

TABLE 1

| Gene Name | Sense Primer (5'→3') | SEQ ID NO: | Antisense (5'→3') Primer | SEQ ID NO: |
|---|---|---|---|---|
| β-actin | TGGATAAGCTGCAGTCACAG | 2 | GCGTAGAGGTCCTCCCTGATGT | 3 |
| IFN-ß | AGTTGCCTGGGACTCCTCAA | 4 | CCTCAGGGACCTCAAAGTTCAT | 5 |
| IFN-λ | CCTTAGAGGCTGAGCTAGACTTGAC | 6 | AGCCTGAAGTTCGACGTGGATG | 7 |
| Mx1 | GAGGTGGACCCCGAAGGA | 8 | CACCAGATCCGGCTTCGT | 9 |
| OAS1 | CCAACAGGTTCAGACAGCCT | 10 | GAGGAGCCACCCTTCACAAC | 11 |
| RNaseL | GCAGCCGAGCCAACGATA | 12 | AGCTCCCGTCGCTCTCACT | 13 |
| PKR | CCCTGCACTTCTAGCCATCT | 14 | CGACCACTGGCCATTTCTTTC | 15 |
| RIG-I | TATCCGAGCAGCAGGCTTTG | 16 | CTCGTTGCTGGGATCTATGGCC | 17 |
| TLR2 | ACATGAAGATGATGTGGGCC | 18 | TAGGAGTCCTGCTCACTGTA | 19 |
| TLR3 | TAGAGACATGGATTGCTCCC | 20 | AACTTCTGGAATGCAGGTCC | 21 |
| TLR4 | CTCTGCCTTCACTACAGAGA | 22 | CTCTGCCTTCACTACAGAGA | 23 |
| NOD1 | CTGTCGTCAACACCGATCCA | 24 | CCAGTTGGTGACGCAGCTT | 25 |
| NOD2 | GAGCGCATCCTCTTAACTTTCG | 26 | ACGCTCGTGATCCGTGAAC | 27 |
| MCP-1 | ACAGAAGAGTCACCAGCAGCAA | 28 | GCCCGCGATGGTCTTG | 29 |
| IL-6 | TCCATAAGCTGCAGTCACAG | 30 | ATTATCCGAATGGCCCTCAG | 31 |
| IL-8 | GCTCTCTGTGAGGCTGCAGTT | 32 | TTTATGCACTGGCATCGAAGTT | 33 |
| IL-12 | AGTTCCAGGCCATGAATGCA | 34 | TGGCACAGTCTCACTGTTGA | 35 |
| IL-18 | TGAACCGGAAGACAATTGCATCAG | 36 | CCAGGTCTTCATCGTTTTCAGCTAC | 37 |
| TNFα | CGACTCAGTGCCGAGATCAA | 38 | CCTGCCCAGATTCAGCAAAG | 39 |
| A20 | CCTCCCTGGAAAGCCAGAA | 40 | GTGCCACAAGCTTCCTCACTT | 41 |
| BCL-3 | CGACGCGGTGGACATTAAG | 42 | ACCATGCTAAGGCTGTTGTTTTC | 43 |
| Tollip | TACCGTGGGCCGTCTCA | 44 | CCGTAGTTCTTCGCCAACTTG | 45 |
| IRAK-M | TGGAGCAGCCTTGAATCCTT | 46 | TGGATAACACGTTTGGGAATCTT | 47 |
| MKP-1 | AACGAGGGTCAGGCTTTTCC | 48 | TCCCCAATGTGCTGAGTTCAG | 49 |
| SIGIRR | ATGTGAAGTGTCGGCTCAATGT | 50 | TTCATCTCCACCTCCCCATACT | 51 |

1-2 Results

[Expression Analysis of Cytokine-Related Factors in Poly I:C-Stimulated PIE Cell Line]

As a result of the analysis of the mRNA expression levels of the 24 cytokine-related factor genes in the poly I:C-stimulated PIE cell line, the expression levels of two anti-viral factors (IFN-β and Mx1) increased significantly at and after three hours of the poly I:C stimulation. In particular, the expression level of IFN-β was the highest at the third hour after the poly I:C stimulation, and the expression level of Mx1 was the highest at the 12th hour after the poly I:C stimulation (see FIGS. 1A and B).

From the results, it was determined to use the expression level of IFN-β at the third hour after the poly I:C stimulation and the expression level of Mx1 at the 12th hour after the poly I:C stimulation as indicators for selecting the Lacto-bacillus strains of this case.

Example 2. Selection of Lactobacillus Strains of This Case Using Antiviral Activity as Indicator Using the expression levels of the two antiviral factors (IFN-β and Mx1) as indicators, the Lactobacillus strains of this case were selected.

2-1 Method

[Preparation of Lactobacillus salivarius-Containing Solutions]

Each of 116 Lactobacillus salivarius strains isolated from a porcine intestinal tract was inoculated in MRS liquid medium (manufactured by Difco), cultured at 37° C. for 16 hours, then passaged three times and washed with PBS. After heat sterilization at 72° C. for 1.5 hours, the cells were washed twice with PBS and re-suspended in DMEM liquid medium at a concentration of $2.5 \times 10^9$ cells/mL, and 116 Lactobacillus salivarius strain-containing solutions were thus prepared.

[Selection of Lactobacillus Strains of This Case]

The PIE cell line was stimulated with the prepared 116 Lactobacillus salivarius strain-containing solutions and then stimulated with poly I:C, and the *Lactobacillus* strains of this case were selected using the expression levels of the two antiviral factors (IFN-β and Mx1) as indicators. Specifically, the analysis was conducted according to the following procedures [1] to [4].

[1] The PIE cell line was seeded in 12-well plates coated with type I collagen (manufactured by Sumitomo Bakelite Co., Ltd.) at $3 \times 10^4$ cells/well and cultured in DMEM liquid medium for three days.

[2] The prepared 116 *Lactobacillus salivarius* strain-containing solutions were added to the medium each at $5.0 \times 10^7$ cells/mL per well, and the cells were cultured (stimulated) for two days. As a control which was not stimulated with the *Lactobacillus salivarius* strains, the PIE cell line was cultured similarly in DMEM liquid medium which did not contain the *Lactobacillus salivarius* strains.

[3] The medium was removed, and the cells were washed twice with PBS. Then, the medium was replaced with DMEM liquid medium containing 50 ng/mL poly I:C (catalog number P9582, manufactured by SIGMA), and the cells were cultured for three hours and 12 hours and thus stimulated with poly I:C. As controls which were not stimulated with poly I:C, the PIE cell line was cultured similarly in poly I:C-free DMEM liquid medium.

[4] After removing the medium, the procedures from the collection of the total RNA of the cells to the analysis of the mRNA expression levels of the genes of the two antiviral factors (IFN-β and Mx1) were conducted according to the procedures [3] to [5] in the section [Expression Analysis of Cytokine-Related Factors in Poly I:C-Stimulated PIE Cell Line] in Example 1 above. The expression levels of IFN-β and the expression levels of Mx1 with the stimulation with the *Lactobacillus salivarius* strains were calculated based on the equation ([the mRNA expression level of IFN-β gene or Mx1 gene/the mRNA expression level of β-actin gene] with the stimulation with the *Lactobacillus salivarius* strain before the stimulation with poly I:C/[the mRNA expression level of IFN-β gene or Mx1 gene/the mRNA expression level of β-actin gene] with the stimulation with poly I:C) (see the vertical axis in FIG. 2).

2-2 Results

Figures 1A, 1B, 2:
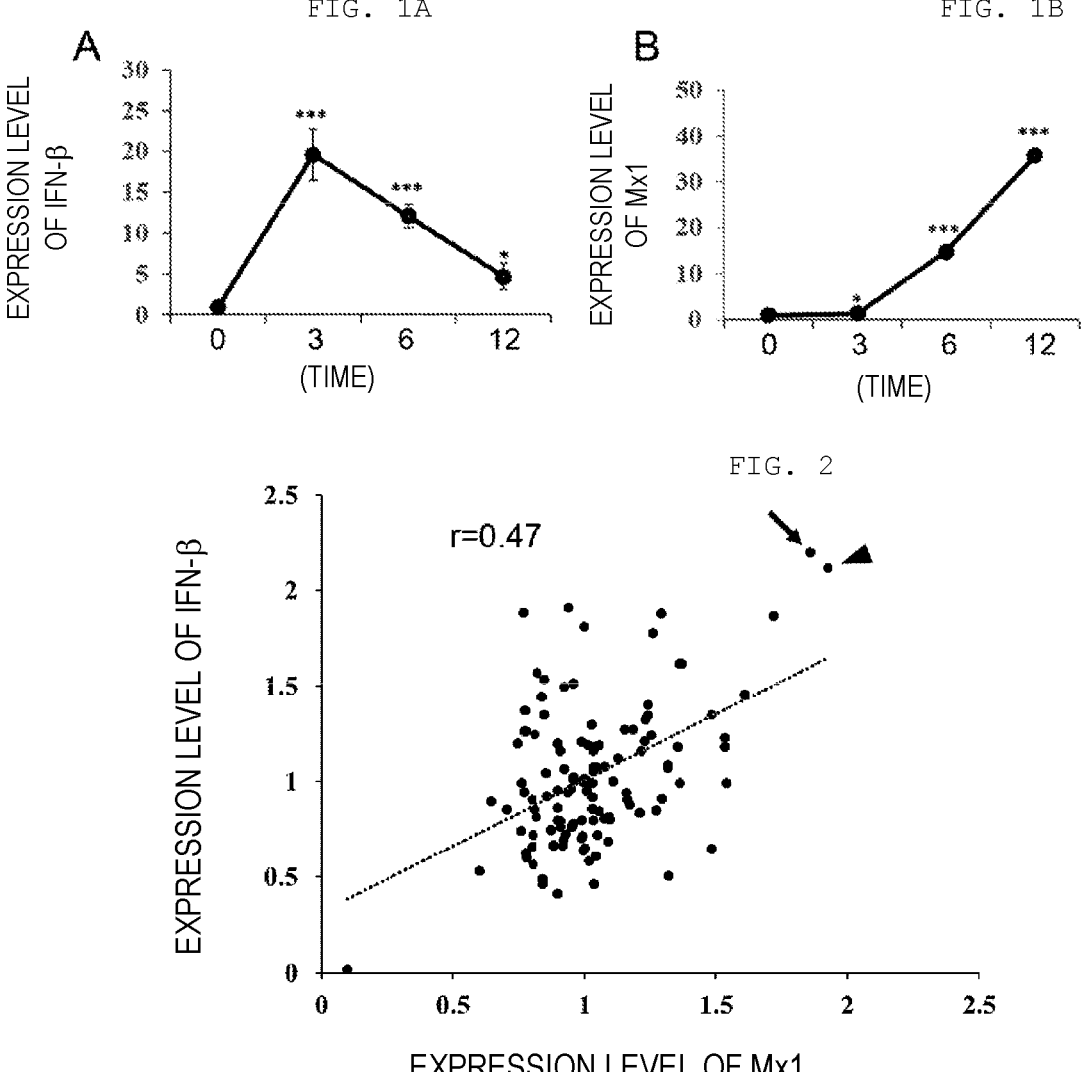
FIG. 2—A figure showing the results of analysis of the expression levels of two antiviral factors (IFN-β [vertical axis] and Mx1 [horizontal axis]) in the PIE cell line stimulated with 116 *Lactobacillus salivarius* strains before stimulation with poly I:C. Each dot (•) in the figure shows a *Lactobacillus salivarius* strain. The arrow in the figure indicates strain #35 of this case, and the arrowhead in the figure indicates strain #58 of this case.

As a result of the analysis of the expression levels of the two antiviral factors (IFN-β and Mx1) in the PIE cell line which was stimulated with the 116 *Lactobacillus salivarius* strains before the stimulation with poly I:C, the expression levels with the stimulation with *Lactobacillus salivarius* strain #35 (in the present specification, sometimes called "strain #35 of this case") and *Lactobacillus salivarius* strain #58 (in the present specification, sometimes called "strain #58 of this case") were the highest (see the arrow and the arrowhead in FIG. 2).

From the results, strain #35 of this case and strain #58 of this case were selected as the *Lactobacillus* strains of this case. 1) Strain #35 of this case is a *Lactobacillus salivarius* strain having 16S rRNA gene having the nucleotide sequence of SEQ ID NO: 1 and has the following features. Strain #35 of this case was deposited for an international deposit at NITE Patent Microorganisms Depositary (NPMD), National Institute of Technology and Evaluation (NITE) (address: #122, 2-5-8 Kazusakamatari, Kisarazu-shi, Chiba 292-0818, Japan) on May 19, 2020 under international deposit accession number NITE BP-03218.
(a) Cell Morphology
    Shape: *bacillus*, sporulation: (−), motility: (−)
(b) Colony Morphology (The strain was smeared on an MRS agar plate and aerobically cultured at 37° C. for 24 hours, and the colony shape was observed.)

(1) Gram stain: (+)
    (2) Gas production: (−)
    (3) Catalase activity: (−)
    (4) Indole production: (−)
    (5) Response to oxygen: facultatively anaerobic
    (6) Optimum growth temperature: 37 to 40° C.
    (7) Optimum growth pH: pH 5.5 to 5.8
2) Strain #58 of this case is a *Lactobacillus salivarius* strain having 16S rRNA gene having the nucleotide sequence of SEQ ID NO: 1 and has the following features. Strain #58 of this case was deposited for an international deposit at NITE Patent Microorganisms Depositary (NPMD), National Institute of Technology and Evaluation (NITE) (address: #122, 2-5-8 Kazusakamatari, Kisarazu-shi, Chiba 292-0818, Japan) on May 19, 2020 under international deposit accession number NITE BP-03219.
(a) Cell Morphology
    Shape: *bacillus*, sporulation: (−), motility: (−)
(b) Colony Morphology (The strain was smeared on an MRS agar plate and aerobically cultured at 37° C. for 24 hours, and the colony shape was observed.)
    (1) Gram stain: (+)
    (2) Gas production: (−)
    (3) Catalase activity: (−)
    (4) Indole production: (−)
    (5) Response to oxygen: facultatively anaerobic
    (6) Optimum growth temperature: 37 to 40° C.
    (7) Optimum growth pH: pH 5.5 to 5.8

Example 3. Evaluation of Immunomodulatory Potential of *Lactobacillus* Strains of This Case The PIE cell line was stimulated with selected strain #35 of this case or strain #58 of this case only, and the immune response of the cells was analyzed.
3-1 Method
The immune response of the cells was analyzed according to the following procedures [1] to [3].

[1] The PIE cell line was seeded in 12-well plates coated with type I collagen (manufactured by Sumitomo Bakelite Co., Ltd.) at $3 \times 10^4$ cells/well and cultured in DMEM liquid medium for three days.

[2] Strain #35 of this case and strain #58 of this case were added to the medium each at $5.0 \times 10^7$ cells/mL per well, and the cells were cultured (stimulated) for 0 hour (unstimulated), three hours, six hours, 12 hours, 24 hours and 48 hours. As a control which was not stimulated with the strains, the PIE cell line was cultured similarly in DMEM liquid medium which did not contain the strains.

[3] After removing the medium, the procedures from the collection of the total RNA of the cells to the analysis of the mRNA expression levels of the genes of five receptors (TLR2, TLR3, TLR4, NOD1 and NOD2) and the mRNA expression levels of the genes of seven antiviral factors (IFN-β, IFN-λ, Mx1, OAS1, RNaseL, PKR and RIG-I) were conducted according to the procedures [3] to [5] in the section [Expression Analysis of Cytokine-Related Factors in Poly I:C-Stimulated PIE Cell Line] in Example 1 above. The expression levels of the receptors (see FIG. 3) and the expression levels of the antiviral factors (see FIGS. 4 and 5) with the stimulation with strain #35 of this case or strain #58 of this case were calculated based on the equation ([the mRNA expression level of the receptor gene or the antiviral factor gene/the mRNA expression level of β-actin gene] with the stimulation with strain #35 of this case or strain #58 of this case/[the mRNA expression level of the receptor gene or the antiviral factor gene/the mRNA expression level of β-actin gene] without the stimulation with the strains (0 hour)).

3-2 Results

Figures 3A, 3B, 3C, 3D, 3E:
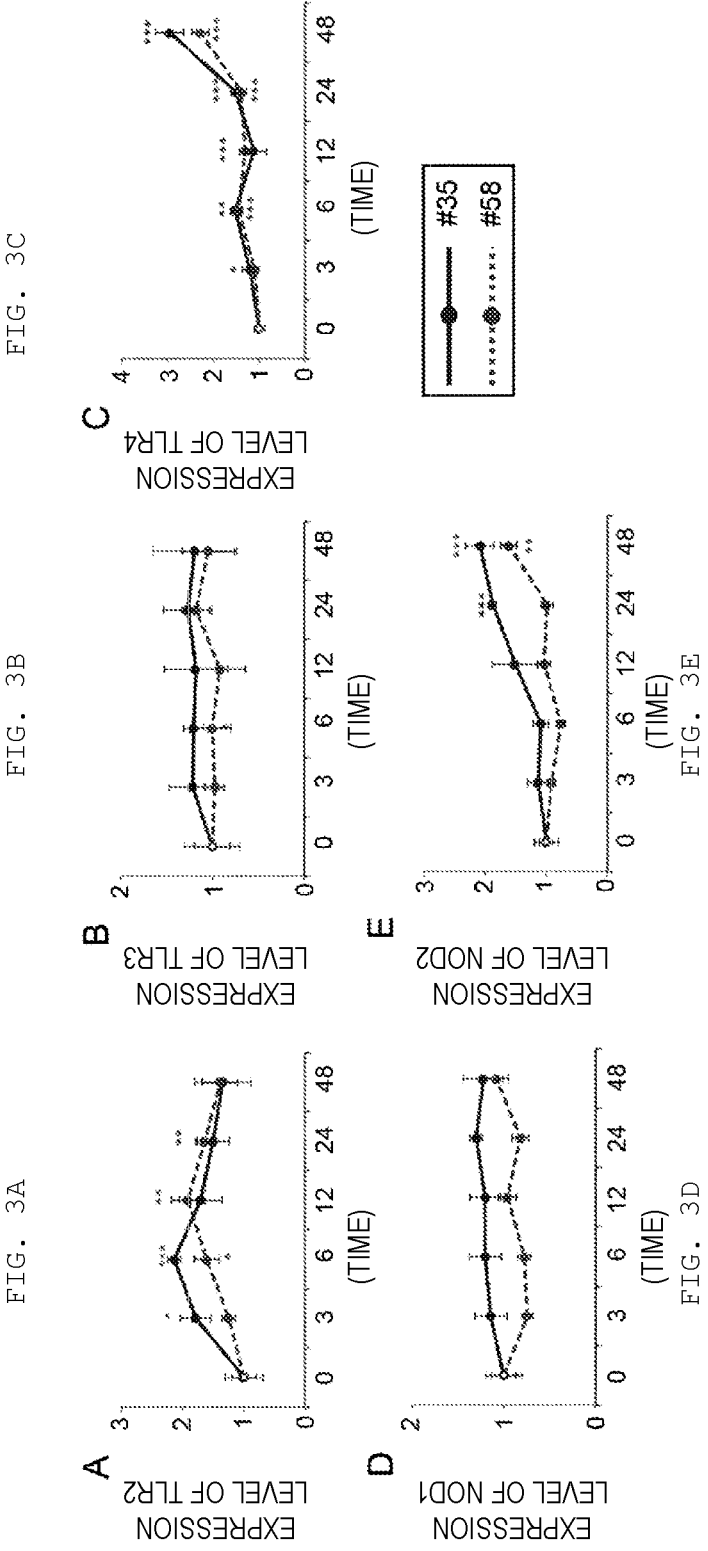
FIG. 3—A figure showing the results of analysis of the expression levels of five receptors (TLR2 [FIG. 3A], TLR3 [FIG. 3B], TLR4 [FIG. 3C], NOD1 [FIG. 3D] and NOD2 [FIG. 3E]) in the PIE cell line stimulated with strain #35 of this case ("#35" in the figure) or strain #58 of this case ("#58" in the figure). In the figure, "*", "" and "*" indicate statistically significant differences ($p<0.05$, $p<0.01$ and $p<0.001$) from the results at 0 hour.

As a result of the analysis of the expression levels of the five receptors in the PIE cell line which was stimulated with strain #35 of this case or strain #58 of this case, the expression levels of three receptors which recognize the outer layer component of cells of gram-positive bacteria (TLR2, TLR4 and NOD2) increased significantly (see FIG. 3). Specifically, the expression level of TLR2 increased for six hours and 12 hours after the stimulation with strain #35 of this case and strain #58 of this case, respectively, reached the peak and then decreased, while the expression levels of TLR4 and NOD2 increased at least for 48 hours after the stimulation with strain #35 of this case and strain #58 of this case (see FIG. 3).

The results suggest that a bacterial cell membrane component constituting strain #35 of this case or strain #58 of this case may be recognized by the three receptors as a ligand.

Figures 4A, 4B, 4C, 4D:
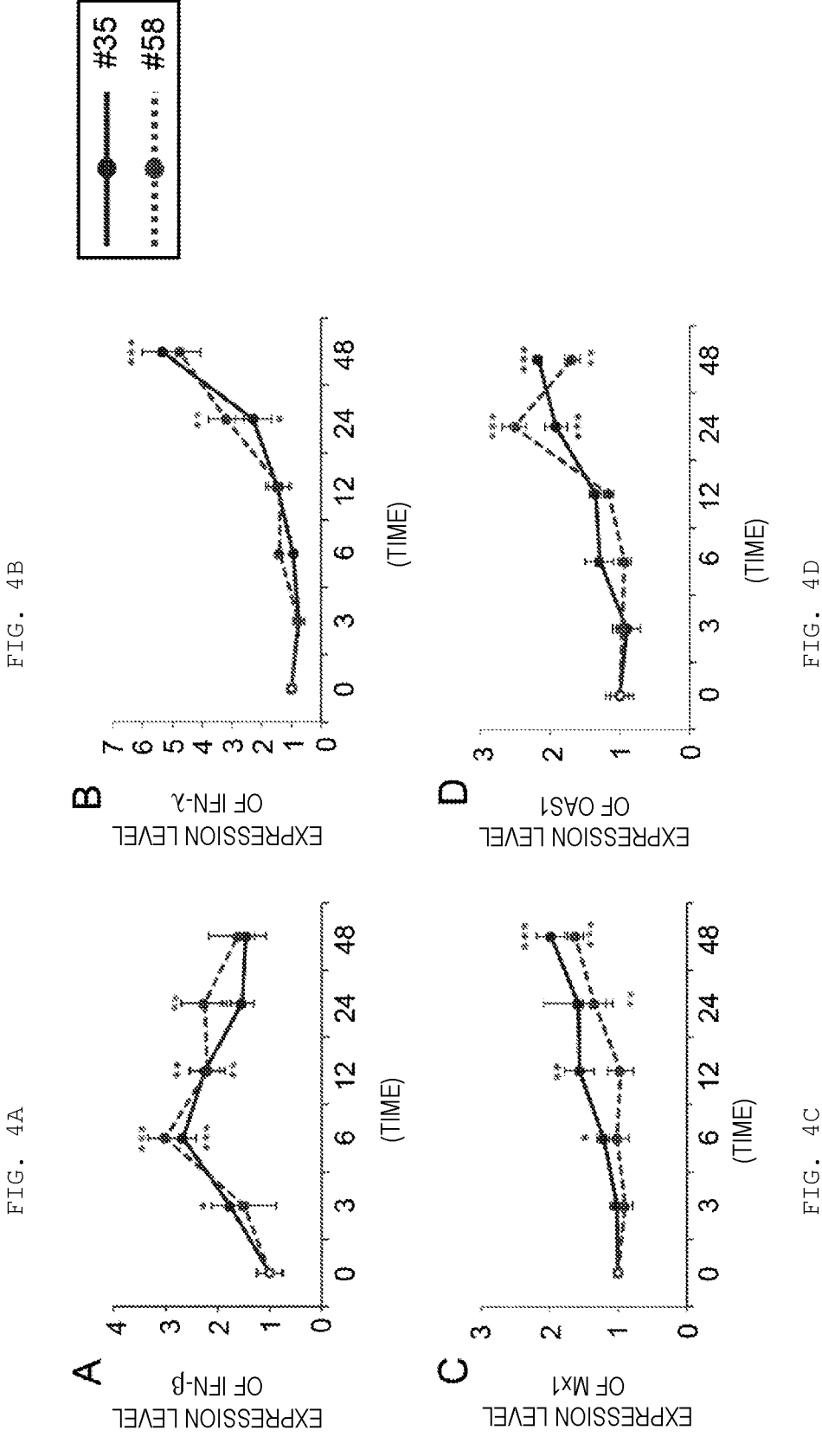
FIG. 4—A figure showing the results of analysis of the expression levels of four antiviral factors (IFN-β [FIG. 4A], IFN-λ [FIG. 4B], Mx1 [FIG. 4C] and OAS1 [FIG. 4D]) in the PIE cell line stimulated with strain #35 of this case ("#35" in the figure) or strain #58 of this case ("#58" in the figure). In the figure, "*", "" and "*" indicate statistically significant differences ($p<0.05$, $p<0.01$ and $p<0.001$) from the results at 0 hour.
Figures 5A, 5B, 5C:
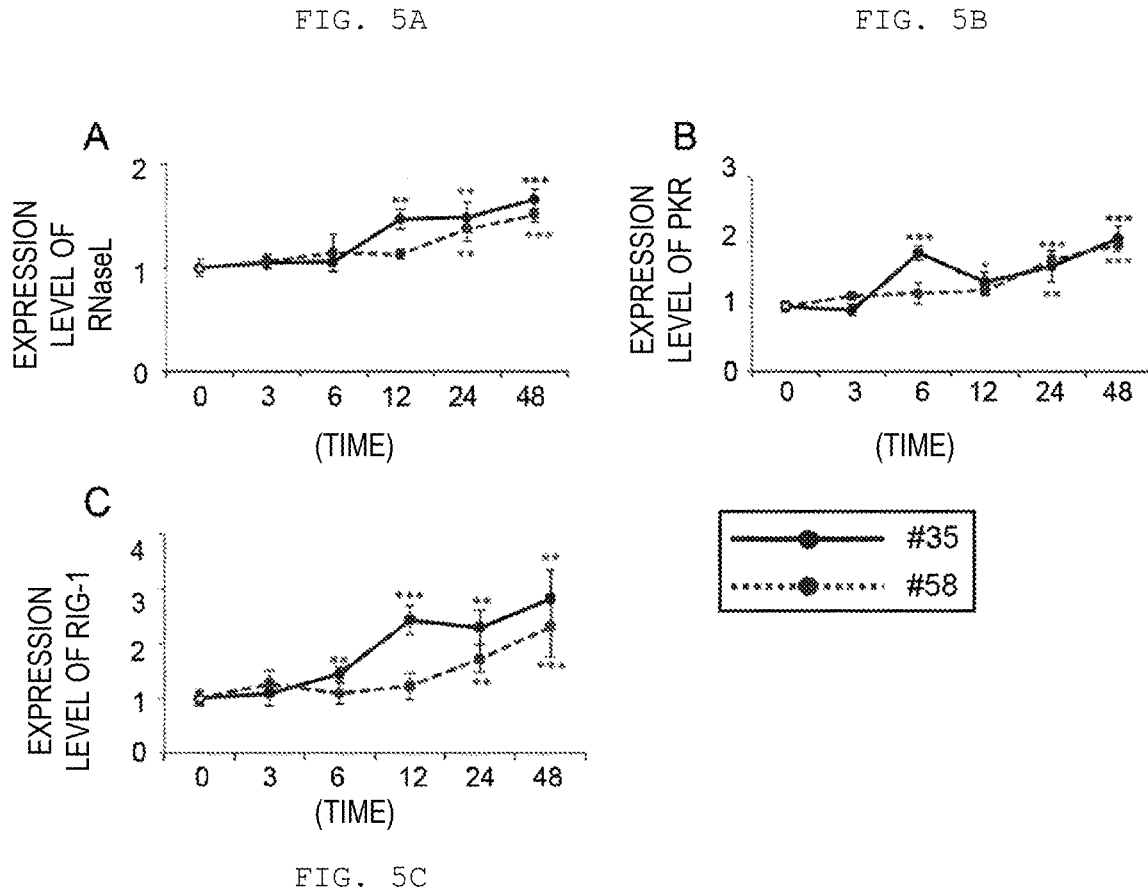
FIG. 5—A figure showing the results of analysis of the expression levels of three antiviral factors (RNaseL [FIG. 5A], PKR [FIG. 5B] and RIG-I [FIG. 5C]) in the PIE cell line stimulated with strain #35 of this case ("#35" in the figure) or strain #58 of this case ("#58" in the figure). In the figure, "" and "*" indicate statistically significant differences ($p<0.01$ and $p<0.001$) from the results at 0 hour.

Moreover, as a result of the analysis of the expression levels of the seven antiviral factors (IFN-β, IFN-λ, Mx1, OAS1, RNaseL, PKR and RIG-I) in the PIE cell line which was stimulated with strain #35 of this case or strain #58 of this case, the expression levels of all the antiviral factors, namely the two types of IFN (IFN-β and IFN-λ) and the five IFN-inducible factors (Mx1, OAS1, RNaseL, PKR and RIG-I), increased significantly (see FIGS. 4 and 5). In particular, the expression level of IFN-β increased remarkably at the sixth hour after the stimulation with strain #35 of this case or strain #58 of this case, and the expression level of IFN-λ increased remarkably at the 48th hour after the stimulation with strain #35 of this case or strain #58 of this case (see FIG. 4).

The results show that strain #35 of this case or strain #58 of this case increased the expression levels of IFN and the factors induced by IFN and that, as a result, the reactivity of the PIE cell line to the virus increased. In particular, because it is known that TLR3 and RIG-I recognize the double-stranded RNA in double-stranded RNA viruses such as rotaviruses and exhibit antiviral action and that Mx1 acts on suppression of the multiplication of single-stranded RNA or DNA viruses, strain #35 of this case and strain #58 of this case are well expected to enhance the antiviral immune response.

Example 4. Evaluation 1 of Immunomodulatory Potential of *Lactobacillus* Strains of This Case on Double-Stranded RNA Model Virus To evaluate the immunomodulatory potential of strain #35 of this case and strain #58 of this case on a double-stranded RNA model virus, the PIE cell line was stimulated with strain #35 of this case or strain #58 of this case before stimulation with poly I:C, and the expression of antiviral factors was analyzed.

4-1 Method

The immune response of the cells was analyzed according to the following procedures [1] to [4].

[1] The PIE cell line was seeded in 12-well plates coated with type I collagen (manufactured by Sumitomo Bakelite Co., Ltd.) at $3\times10^4$ cells/well and cultured in DMEM liquid medium for three days.

[2] Strain #35 of this case and strain #58 of this case were added to the medium each at $5.0\times10^7$ cells/mL per well, and the cells were cultured (stimulated) for 48 hours. As a control which was not stimulated with the strains, the PIE cell line was cultured similarly in DMEM liquid medium which did not contain the strains.

[3] The medium was removed, and the cells were washed twice with PBS. Then, the medium was replaced with DMEM liquid medium containing 50 ng/mL poly I:C (catalog number P9582, manufactured by SIGMA), and the cells were cultured for 12 hours and thus stimulated with poly I:C. As controls which were not stimulated with poly I:C, the PIE cell line was cultured similarly in poly I:C-free DMEM liquid medium.

[4] After removing the medium, the procedures from the collection of the total RNA of the cells to the analysis of the mRNA expression levels of the genes of five antiviral factors (IFN-β, Mx1, OAS1, RNaseL and PKR) were conducted according to the procedures [3] to [5] in the section [Expression Analysis of Cytokine-Related Factors in Poly I:C-Stimulated PIE Cell Line] in Example 1 above. The expression levels of the antiviral factors with the stimulation with strain #35 of this case or strain #58 of this case (see FIG. 6) were calculated based on the equation ([the mRNA expression level of the antiviral factor gene/the mRNA expression level of β-actin gene] with the stimulation with strain #35 of this case or strain #58 of this case before the stimulation with poly I:C/[the mRNA expression level of the antiviral factor gene/the mRNA expression level of β-actin gene] with the stimulation with poly I:C). As controls for comparison, the expression levels of the antiviral factors without the stimulation with the strains and poly I:C were also calculated (see "POLY(I:C)-" in FIG. 6).

4-2 Results

Figures 6A, 6B, 6C, 6D, 6E:
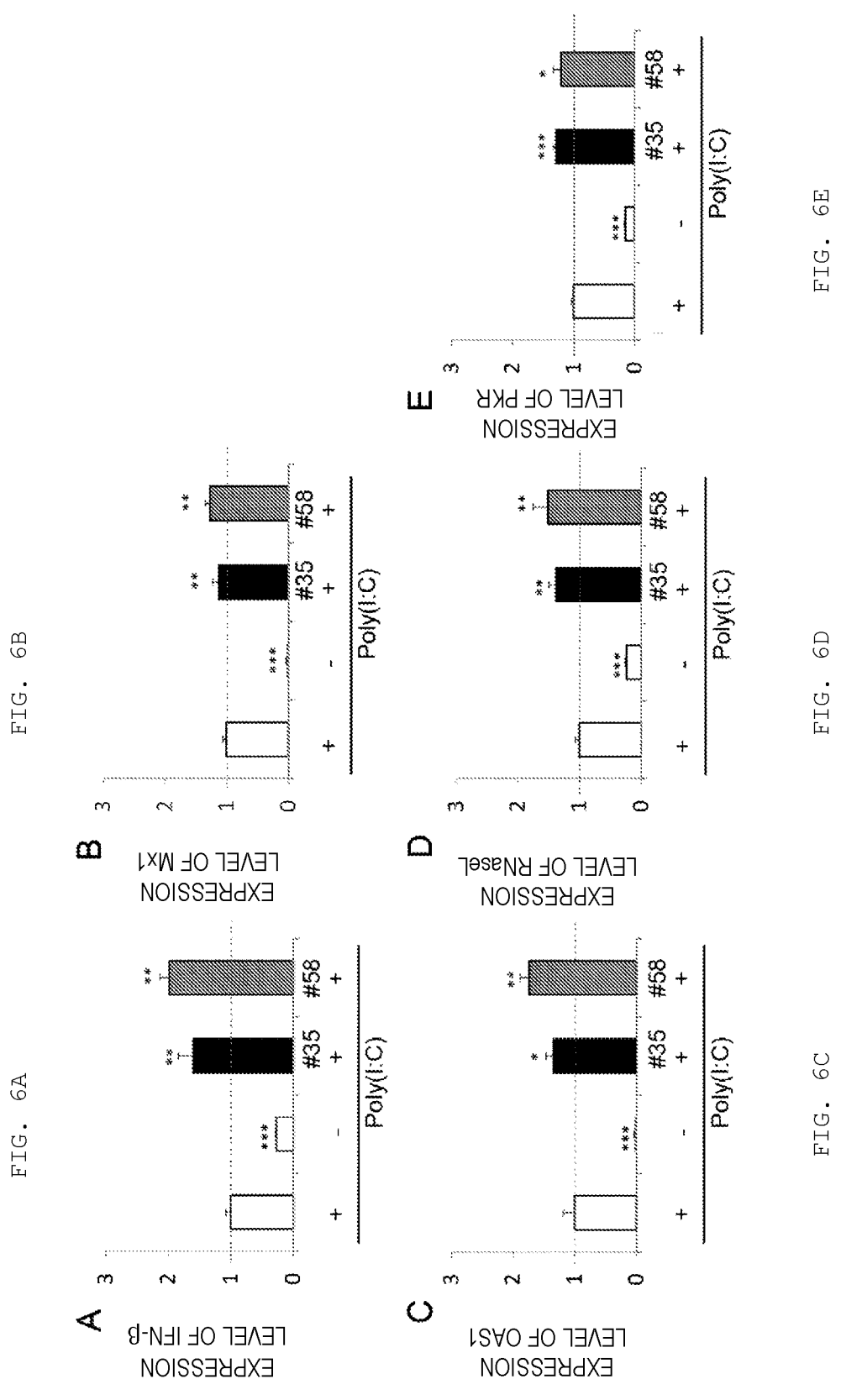
FIG. 6—A figure showing the results of analysis of the expression levels of five antiviral factors (IFN-β [FIG. 6A], Mx1 [FIG. 6B], OAS1 [FIG. 6C], RNaseL [FIG. 6D] and PKR [FIG. 6E]) in the PIE cell line stimulated with strain #35 of this case ("#35" in the figure) or strain #58 of this case ("#58" in the FIG. before stimulation with poly I:C. In the figure, "*", "**" and indicate statistically significant differences ($p<0.05$, $p<0.01$ and $p<0.001$) from the results of the case with stimulation only with poly I:C ("POLY(I:C)+" in the figure).

The expression levels of the five antiviral factors (IFN-β, Mx1, OAS1, RNaseL and PKR) in the PIE cell line which was stimulated with strain #35 of this case or strain #58 of this case before the stimulation with poly I:C increased significantly compared to the expression levels in the PIE cell line which was not stimulated with the strains and which was stimulated with poly I:C (see FIG. 6).

The results show that strain #35 of this case or strain #58 of this case has the action of enhancing the IFN-β production in response to poly I:C stimulation and the action of enhancing the expression of the IFN-inducible factors (Mx1, OAS1, RNaseL and PKR). Accordingly, it was suggested that strain #35 of this case or strain #58 of this case is useful for infection with a double-stranded RNA virus.

Example 5. Evaluation 2 of Immunomodulatory Potential of *Lactobacillus* Strains of This Case on Double-Stranded RNA Model Virus A20/TNFAIP3 is known to be a negative regulator which plays an especially important role in viral infection, and it has been reported that infection with a rotavirus is suppressed significantly in cells in which the expression of A20 has been knocked down (see document "Vet Res. 2011 Nov. 3; 42:111. doi: 10.1186/1297-9716-42-111."). Moreover, it has been reported that Tollip (Toll-interacting protein) is a negative regulator which inhibits phosphorylation through interaction with IRAK-1 and which negatively regulates the signaling of TLR2 or TLR4 and is involved in the regulation of the expression of IRF3 (interferon regulatory factor 3) involved in the expression of IFN-β or IFN-λ (sed document "Fish Shellfish Immunol. 2015 December; 47(2):807-16."). Thus, to analyze the mechanism of the action of enhancing the expression of an antiviral factor of strain #35 of this case or strain #58 of this case, the expression of downregulators of an antiviral factor, A20 and Tollip, was analyzed.

5-1 Method

The immune response of the cells was analyzed according to the following procedures [1] to [4].

[1] The PIE cell line was seeded in 12-well plates coated with type I collagen (manufactured by Sumitomo Bakelite Co., Ltd.) at $3 \times 10^4$ cells/well and cultured in DMEM liquid medium for three days.

[2] Strain #35 of this case and strain #58 of this case were added to the medium each at $5.0 \times 10^7$ cells/mL per well, and the cells were cultured (stimulated) for 48 hours. As a control which was not stimulated with the strains, the PIE cell line was cultured similarly in DMEM liquid medium which did not contain the strains.

[3] The medium was removed, and the cells were washed twice with PBS. Then, the medium was replaced with DMEM liquid medium containing 50 ng/mL poly I:C (catalog number P9582, manufactured by SIGMA), and the cells were cultured for three hours, six hours or 12 hours and thus stimulated with poly I:C. As controls which were not stimulated with poly I:C, the PIE cell line was cultured similarly in poly I:C-free DMEM liquid medium.

[4] After removing the medium, the procedures from the collection of the total RNA of the cells to the analysis of the mRNA expression levels of A20 gene and Tollip gene were conducted according to the procedures [3] to [5] in the section [Expression Analysis of Cytokine-Related Factors in Poly I:C-Stimulated PIE Cell Line] in Example 1 above. The expression levels of A20 and the expression levels of Tollip with the stimulation with strain #35 of this case or strain #58 of this case (see FIG. 7) were calculated based on the equation ([the mRNA expression level of A20 gene or Tollip gene/the mRNA expression level of β-actin gene] with the stimulation with strain #35 of this case or strain #58 of this case before the stimulation with poly I:C/[the mRNA expression level of A20 gene or Tollip gene/the mRNA expression level of β-actin gene] with the stimulation with poly I:C). As controls for comparison, the expression level of A20 and the expression level of Tollip without the stimulation with the strains and poly I:C were also calculated (see "POLY(I:C)-" in FIG. 7).

5-2 Results

Figures 7A, 7B, 7C:
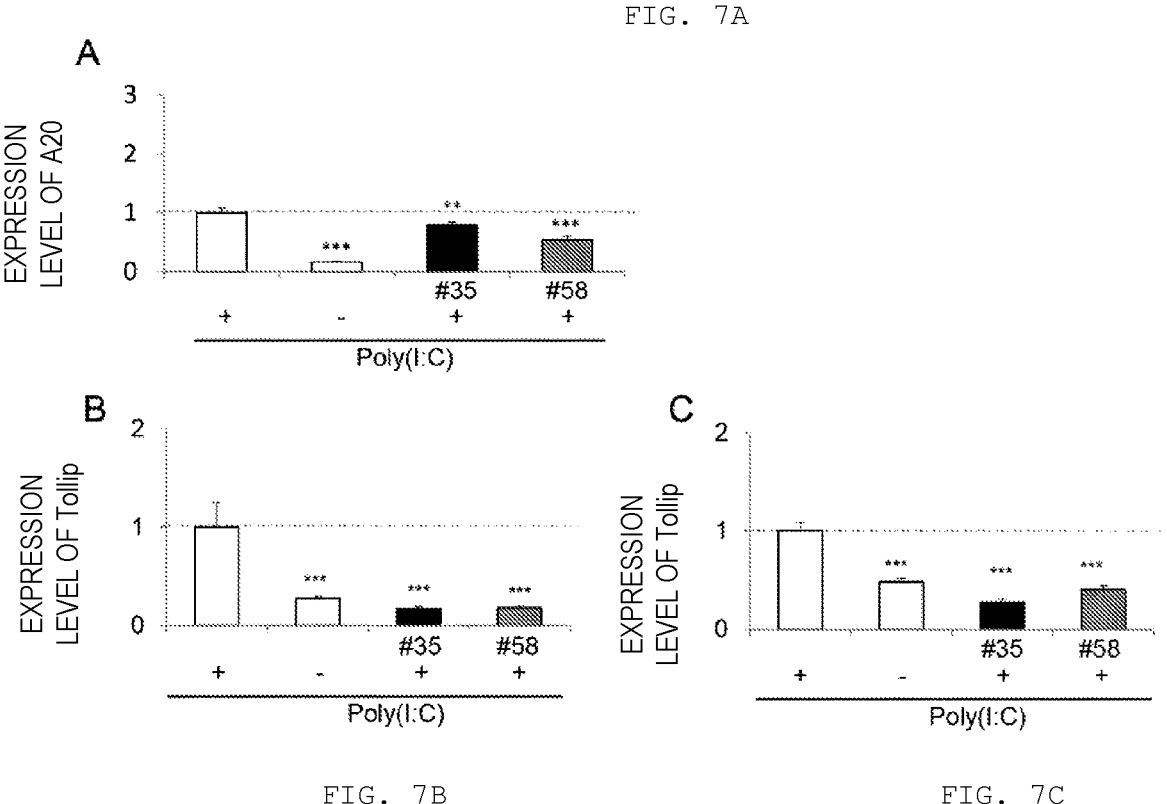

The expression levels of A20 and Tollip in the PIE cell line which was stimulated with strain #35 of this case or strain #58 of this case before the stimulation with poly I:C decreased significantly compared to the expression levels in the PIE cell line which was not stimulated with the strains and which was stimulated with poly I:C (see FIG. 7).

Taking the results of Example 4 above also into consideration, the results show that, when strain #35 of this case or strain #58 of this case is administered to cells infected with a double-stranded RNA virus, the expression level of a downregulator (negative regulator) of an antiviral factor such as A20 and Tollip decreases, and the action of enhancing the expression of the antiviral factor is exhibited.

Example 6. Examination of Viral Infection-Reducing Effect of *Lactobacillus* Strains of This Case Because it was shown that strain #35 of this case and strain #58 of this case enhance the antiviral immune response, a rotavirus infection test was conducted to see that the strains have the effect of reducing viral infection.

6-1 Materials and Methods

[Tested Viral Strain]

Livestock infectious group A rotavirus strain OSU found in pigs as hosts which was used was provided from National Institute of Animal Health, National Agriculture and Food Research Organization.

[Preparation of Active Rotavirus Solution]

To 200 μL of rotavirus strain OSU-containing DMEM liquid medium (containing high glucose, L-glutamine and sodium pyruvate; manufactured by GIBCO), 2 μL of 1 mg/mL purified trypsin (T8003-1G Type I, manufactured by SIGMA) was added (the final trypsin concentration of 10 μg/mL). After mixing well, the mixture was incubated at 37° C. for 30 minutes for trypsin treatment, and thus an active rotavirus solution was prepared.

[Rotavirus Infection Test and Indirect Fluorescent Antibody Assay]

The rotavirus infection test and the subsequent indirect fluorescent antibody assay using an anti-rotavirus antibody were conducted according to the following procedures [1] to [7].

[1] The PIE cell line was seeded in 96-well plates coated with type I collagen (manufactured by Sumitomo Bakelite Co., Ltd.) at $3 \times 10^4$ cells/mL and cultured in DMEM liquid medium for eight days.

[2] Strain #35 of this case and strain #58 of this case were added to the medium each at 100 MOI (multiplicity of infection) per well, and the cells were cultured (stimulated) for 48 hours. As a control which was not stimulated with the strains, the PIE cell line was cultured similarly in DMEM liquid medium which did not contain the strains.

[3] The cells were washed three times with FCS-free DMEM liquid medium, and the active rotavirus solution prepared according to the method described in the section [Preparation of Active Rotavirus Solution] above was added at 100 μL (corresponding to 1 MOI) per well, followed by incubation under the conditions of 5% $CO_2$/20% $O_2$ at 37° C. for 16 hours.

[4] The active rotavirus solution was removed, and 80% acetone solution at 4° C. was added at 100 μL per well. The cells were incubated at 4° C. for 20 minutes, and the cells were thus fixed.

[5] The acetone solution was removed, and the cells were washed three times with PBS. Then, primary antibody reaction using a rotavirus A antibody (anti-human strain RVAWa guinea pig serum, provided from National Institute of Animal Health, National Agriculture and Food Research Organization) was conducted. Specifically, the rotavirus A antibody was diluted 800-fold with PBS and dispensed at 50 μL per well, and the cells were incubated at 37° C. for 40 minutes.

[6] After washing the cells three times with PBS, secondary antibody reaction using an ALEXA Fluor™ 488-labeled anti-guinea pig IgG antibody (Cat. ab150185, manufactured by abcam) was conducted. Specifically, the antibody was diluted 400-fold with PBS to 1:400 and dispensed at 50 μL per well, and then the cells were incubated at 37° C. for 40 minutes.

[7] After washing the cells three times with PBS, 30% glycerin-containing PBS was dispensed at 50 μL per well. Then, ALEXA Fluor™ 488-derived fluorescent signals were detected using a fluorescence microscope (IX70-FL manufactured by Olympus Corporation) (see FIG. 8A), and the percentages (%) of the fluorescent signal-positive cells, namely the rotavirus-positive (infected) cells, were calculated (see FIG. 8B).

6-2 Results

First, it was confirmed that ALEXA Fluor™ 488-derived fluorescent signals, namely rotavirus-positive cells, were detected from the PIE cell line incubated with the active rotavirus solution (see the control in FIGS. 8A and B). Next, it was shown that, when the PIE cell line was stimulated with strain #35 of this case or strain #58 of this case before the incubation in the active rotavirus solution, the percentage of the rotavirus-positive cells decreased significantly to 66% and 57%, respectively, compared to the case without the stimulation with the strains (see #35 and #58 in FIGS. 8A and B).

The results show that strain #35 of this case and strain #58 of this case have the effect of reducing (preventing) viral infection.

Example 7. Evaluation 1 of Immunomodulatory Potential of *Lactobacillus* Strains of This Case in Viral Infection To evaluate the immunomodulatory potential of strain #35 of this case and strain #58 of this case in viral infection, the PIE cell line was stimulated with strain #35 of this case or strain #58 of this case and then infected with a rotavirus, and the expression of antiviral factors was analyzed.

7-1 Method

The rotavirus infection test and the subsequent analysis of the expression of antiviral factors were conducted according to the following procedures [1] to [4].

[1] The PIE cell line was seeded in a 96-well plate coated with type I collagen (manufactured by Sumitomo Bakelite Co., Ltd.) at $5 \times 10^4$ cells/well and cultured in DMEM liquid medium for 10 days.

[2] Strain #35 of this case and strain #58 of this case were added to the medium each at 100 MOI per well, and the cells were cultured (stimulated) for 48 hours. As a control which was not stimulated with the strains, the PIE cell line was cultured similarly in DMEM liquid medium which did not contain the strains.

[3] The cells were washed three times with FCS-free DMEM liquid medium, and the active rotavirus solution prepared according to the method described in the section [Preparation of Active Rotavirus Solution] in Example 6 above was added at 100 μL (corresponding to 1 MOI) per well, followed by incubation under the conditions of 5% $CO_2/20\%$ $O_2$ at 37° C. for three hours, six hours or 12 hours.

[4] After removing the active rotavirus solution, the procedures from the collection of the total RNA of the cells to the analysis of the mRNA expression levels of the genes of four antiviral factors (IFN-β, IFN-γ, Mx1 and RNaseL) were conducted according to the procedures [3] to [5] in the section [Expression Analysis of Cytokine-Related Factors in Poly I:C-Stimulated PIE Cell Line] in Example 1 above.

7-2 Results

When the PIE cell line was stimulated with strain #35 of this case or strain #58 of this case before the incubation in the active rotavirus solution, the expression levels of the four antiviral factors (IFN-β [FIG. 9A], IFN-γ [FIG. 9B], Mx1 [FIG. 9C] and RNaseL [FIG. 9D]) increased significantly compared to the case without the stimulation with the strains (see FIG. 9).

The results show that the action of enhancing the expression of an antiviral factor is exhibited when strain #35 of this case or strain #58 of this case is administered to cells infected with a virus.

Example 8. Evaluation 2 of Immunomodulatory Potential of *Lactobacillus* Strains of This Case in Viral Infection To evaluate the immunomodulatory potential of strain #35 of this case and strain #58 of this case in viral infection, the PIE cell line was stimulated with strain #35 of this case or strain #58 of this case and then infected with a rotavirus, and the expression of A20 and Tollip, which down-regulate the expression of an antiviral factor, was analyzed.

8-1 Method

The rotavirus infection test and the subsequent analysis of the expression of A20 and Tollip were conducted according to the following procedures [1] to [4].

[1] The PIE cell line was seeded in a 96-well plate coated with type I collagen (manufactured by Sumitomo Bakelite Co., Ltd.) at $3 \times 10^4$ cells/mL and cultured in DMEM liquid medium for eight days.

[2] Strain #35 of this case and strain #58 of this case were added to the medium each at 100 MOI per well, and the cells were cultured (stimulated) for 48 hours. As a control which was not stimulated with the strains, the PIE cell line was cultured similarly in DMEM liquid medium which did not contain the strains.

[3] The cells were washed three times with FCS-free DMEM liquid medium, and the active rotavirus solution prepared according to the method described in the section [Preparation of Active Rotavirus Solution] in Example 6 above was added at 100 μL (corresponding to 1 MOI) per well, followed by incubation under the conditions of 5% $CO_2/20\%$ $O_2$ at 37° C. for three hours, six hours or 12 hours.

[4] After removing the active rotavirus solution, the procedures from the collection of the total RNA of the cells to the analysis of the mRNA expression levels of the genes of four antiviral factors (IFN-β, IFN-γ, Mx1 and RNaseL) were conducted according to the procedures [3] to [5] in the section [Expression Analysis of Cytokine-Related Factors in Poly I:C-Stimulated PIE Cell Line] in Example 1 above.

8-2 Results

When the PIE cell line was stimulated with strain #35 of this case or strain #58 of this case before the incubation in the active rotavirus solution, the expression levels of A20 and Tollip decreased significantly compared to the case without the stimulation with the strains (see FIG. 10).

The results show that the expression level of a downregulator of an antiviral factor (for example, A20 and Tollip) decreases and the action of enhancing the expression of the antiviral factor is exhibited when strain #35 of this case or strain #58 of this case is administered to cells infected with a virus.

Example 9. Examination of Effect of Reducing Rotavirus and ETEC Combined Infection of *Lactobacillus* Strains of This Case In actual life, not only single infection with a virus but also combined infection also with a pathogenic bacterium is developed. Thus, a combined infection system of a rotavirus and enterotoxigenic *E. coli* (ETEC) was constructed, and it was first examined whether there was a difference in the efficiency of rotavirus infection between single infection with the rotavirus and combined infection with the rotavirus and ETEC. Next, it was analyzed whether strain #35 of this case and strain #58 of this case were effective also for combined infection with the rotavirus and ETEC.

9-1 Materials and Methods

[Preparation of ETEC-Containing Solution]

An ETEC strain (provided from National Institute of Animal Health, National Agriculture and Food Research Organization) was streaked on an agar plate containing 5% defibrinated sheep blood and cultured at 37° C. for 20 hours. A formed colony was extracted, seeded in 5 mL of tryptone soya broth (TSB) liquid medium (manufactured by Nippon Becton Dickinson Company, Ltd) and stationary cultured at 37° C. for five to eight days for recovering cilia. Then, the bacterium was extracted from the part forming pellicle, seeded in 11 mL of TSB and cultured with shaking at 37° C. for 20 hours. After culturing, the bacterial cells were collected by centrifugation, washed three times with PBS and sterilized by heating at 100° C. for 15 minutes. Then, the bacterial cells were washed with PBS and suspended in DMEM liquid medium at a bacterial cell concentration of $1.5 \times 10^{10}$ cells/mL, and thus an ETEC-containing solution was prepared.

[Rotavirus and ETEC Combined Infection Test and Indirect Fluorescent Antibody Assay]

The rotavirus/ETEC combined infection test and the subsequent indirect fluorescent antibody assay using an anti-rotavirus antibody were conducted according to the following procedures [1] to [4].

[1] The PIE cell line was seeded in a 96-well plate coated with type I collagen (manufactured by Sumitomo Bakelite Co., Ltd.) at $3 \times 10^4$ cells/well and cultured in DMEM liquid medium for eight days.

[2] Strain #35 of this case and strain #58 of this case were added to the medium each at 100 MOI per well, and the cells were cultured (stimulated) for 48 hours. As a control which was not stimulated with the strains, the PIE cell line was cultured similarly in DMEM liquid medium which did not contain the strains.

[3] The cells were washed three times with FCS-free DMEM liquid medium. The active rotavirus solution prepared according to the method described in the section [Preparation of Active Rotavirus Solution] in Example 6 above was added at 100 μL (corresponding to 1 MOI) per well, and the ETEC-containing solution prepared according to the method described in the section [Preparation of ETEC-Containing Solution] above was added at 50 μL (corresponding to 1 MOI) per well, followed by incubation under the conditions of 5% $CO_2$/20% $O_2$ at 37° C. for 16 hours. As controls of single viral infection, the PIE cell line to which the active rotavirus solution alone was added was incubated similarly.

[4] After removing the active rotavirus solution and the ETEC-containing solution, the procedures from fixing of the cells to the indirect fluorescent antibody assay were conducted according to the procedures [4] to [7] in the section [Rotavirus Infection Test and Indirect Fluorescent Antibody Assay] in Example 6 above.

9-2 Results

It was shown that, when the PIE cell line was incubated in the active rotavirus solution and the ETEC-containing solution, the percentage of the rotavirus-positive cells increased significantly compared to the case incubated in the active rotavirus solution alone (see FIG. 11A).

The results show that the efficiency of rotavirus infection in the PIE cell line was increased through the rotavirus/ETEC combined infection compared to the single infection with the rotavirus.

Next, it was shown that, when the PIE cell line was stimulated with strain #35 of this case or strain #58 of this case before the incubation in the active rotavirus solution and the ETEC-containing solution, the percentage of the rotavirus-positive cells decreased significantly compared to the case without the stimulation with the strains (see FIG. 11B).

The results show that strain #35 of this case and strain #58 of this case effectively exhibit a reducing (preventing) effect also on viral infection in virus/pathogenic bacterium combined infection.

Example 10. Evaluation 1 of Immunomodulatory Potential of *Lactobacillus* Strains of this Case in Viral and Bacterial Infection To evaluate the immunomodulatory potential of strain #35 of this case and strain #58 of this case in virus/pathogenic bacterium combined infection, the PIE cell line was stimulated with strain #35 of this case or strain #58 of this case and then infected with a rotavirus, and the expression of antiviral factors and downregulators of an antiviral factor was analyzed.

10-1 Method

The virus/pathogenic bacterium combined infection test and the subsequent analysis of the expression of antiviral factors and downregulators of an antiviral factor were conducted according to the following procedures [1] to [4].

[1] The PIE cell line was seeded in a 96-well plate coated with type I collagen (manufactured by Sumitomo Bakelite Co., Ltd.) at $5 \times 10^4$ cells/well and cultured in DMEM liquid medium for 10 days.

[2] Strain #35 of this case and strain #58 of this case were added to the medium each at 100 MOI per well, and the cells were cultured (stimulated) for 48 hours. As a control which was not stimulated with the strains, the PIE cell line was cultured similarly in DMEM liquid medium which did not contain the strains.

[3] The cells were washed three times with FCS-free DMEM liquid medium. The active rotavirus solution prepared according to the method described in the section [Preparation of Active Rotavirus Solution] in Example 6 above was added at 100 μL (corresponding to 1 MOI) per well, and the ETEC-containing solution prepared according to the method described in the section [Preparation of ETEC-Containing Solution] above was added at 50 μL (corresponding to 1 MOI) per well, followed by incubation under the conditions of 5% $CO_2$/20% $O_2$ at 37° C. for 16 hours. As controls of single viral infection, the PIE cell line to which the active rotavirus solution alone was added was incubated similarly.

[4] After removing the active rotavirus solution and the ETEC-containing solution, the procedures from the collection of the total RNA of the cells to the analysis of the mRNA expression levels of the genes of six antiviral factors (IFN-β, IFN-γ, Mx1, RNaseL, PKR and RIG-1) and the mRNA expression levels of two downregulators of an antiviral factor (A20 and Tollip) were conducted according to the procedures [3] to [5] in the section [Expression Analysis of Cytokine-Related Factors in Poly I:C-Stimulated PIE Cell Line] in Example 1 above.

10-2 Results

When the PIE cell line was stimulated with strain #35 of this case or strain #58 of this case before the incubation in the active rotavirus solution and the ETEC-containing solution, the expression levels of the six antiviral factors (IFN-β, IFN-γ, Mx1, RNaseL, PKR and RIG-1) increased significantly (see FIGS. 12 and 13), and the expression levels of the two downregulators of an antiviral factor (A20 and Tollip) decreased significantly (see FIG. 14), compared to the case without the stimulation with the strains.

The results show that the expression level of a downregulator of an antiviral factor (for example, A20 and Tollip) decreases and the action of enhancing the expression of the antiviral factor is exhibited when a *Lactobacillus* strain of this case (strain #35 of this case or strain #58 of this case) is administered to cells with virus/pathogenic bacterium combined infection.

Example 11. Selection of *Lactobacillus* Strains of this Case Using Ability to Assimilate Wakame as Indicator Regarding the metabolites of bacteria which assimilate seaweeds, especially organic acids produced from algal carbohydrate have been reported to activate the intestinal microorganisms in humans and marine invertebrates (see documents "Front Immunol. 2014 Jan. 14; 4:512." and "NewPhytol. 2010 October; 188(1):82-97."). Furthermore, with respect to prebiotics-related research, it has also been reported that metabolites obtained through microbial fermentation of red algae exhibit an antioxidant or anticoagulation action or an immunomodulatory action (see document "Phytomedicine. 2012 Jun. 15; 19(8-9):797-803."). These reports mean that there are microorganisms which can utilize marine biological materials as substrates and that developmental application thereof creates new value in use. Here, the research team of Jan-Hendrik Hehemann et al. has reported in 2010 that "an enzyme which degrades the algal cell wall in marine bacteria was identified, and the gene encoding the enzyme existed only in the intestinal bacteria in Japanese people" (see document "Anim Sci J. 2011 April; 82(2):274-81."). From this report, it has been speculated that, due to influence of the diet of Japanese people, the newly acquired ability of the intestinal bacteria to degrade the red algae cell wall has spread in the intestinal environment and remains in the gut microbiota of Japanese people. This suggests the emergence of an intestinal bacterium which can activity assimilate seaweeds through the consumption of seaweeds. Thus, the composition of the intestinal microorganisms in the intestinal mucus of a wakame residue-administered pig was analyzed by large-scale analysis of the gut microbiota, and *Lactobacillus* strains having the ability to assimilate wakame were selected using a wakame component-adjusted agar plate.

11-1 Materials and Methods

[Preparation of Wakame Component-Containing Liquid Medium]

Wakame powder in an amount of 0.1 g and 100 mL of Milli-Q water were put into a bottle and autoclaved (121° C., 15 minutes), and thus a 0.1% aqueous wakame solution was prepared. The solution was dispensed into 50-mL tubes and centrifuged (6000 rpm, 20 minutes, 4° C.), and then the supernatants were collected. Sodium chloride and yeast extract were added to the supernatant component (wakame component) at final concentrations of 0.5% and 0.1%, respectively, and thus a 0.1% wakame component-containing liquid medium was prepared. Agar was added to the 0.1% wakame component-containing liquid medium at a final concentration of 1.5%, and 0.1% wakame component-containing agar plates were prepared.

[Culture Test of *Lactobacillus salivarius* Strains in Wakame Component-Containing Liquid Medium]

Onto MRS agar plates, 136 *Lactobacillus salivarius* strains isolated from a porcine intestinal tract were applied. The bacterial strains were added to 5 mL of MRS liquid medium after 72 hours and incubated at 37° C. for 24 hours. The strains were passaged twice in 100 µL of the 0.1% wakame component-containing liquid medium and then adjusted with PBS to OD=0.5, and 5 mL of the 0.1% wakame component-containing liquid medium was added. Then, 100 µL thereof were applied to the 0.1% wakame component-containing agar plates, and the pH of the medium and the colony counts were measured every six hours (see FIG. 15).

11-2 Results

As *Lactobacillus salivarius* strains which proliferate in the wakame component-containing liquid medium, *Lactobacillus salivarius* strain #131 (in the present specification, sometimes called "strain #131 of this case") and *Lactobacillus salivarius* strain #71 (in the present specification, sometimes called "strain #71 of this case") were identified.

1) Like strain #35 of this case and strain #58 of this case, strain #131 of this case is a *Lactobacillus salivarius* strain having 16S rRNA gene having the nucleotide sequence of SEQ ID NO: 1 and has similar features to those of strain #35 of this case and strain #58 of this case. That is, strain #131 of this case has the following features. Strain #131 of this case was deposited for an international deposit at NITE Patent Microorganisms Depositary (NPMD), National Institute of Technology and Evaluation (NITE) (address: #122, 2-5-8 Kazusakamatari, Kisarazu-shi, Chiba 292-0818, Japan) on May 19, 2020 under international deposit accession number NITE BP-03221.

(a) Cell Morphology

Shape: bacillus, sporulation: (−), motility: (−)

(b) Colony Morphology (The strain was smeared on an MRS agar plate and aerobically cultured at 37° C. for 24 hours, and the colony shape was observed.)

(1) Gram stain: (+)
(2) Gas production: (−)
(3) Catalase activity: (−)
(4) Indole production: (−)
(5) Response to oxygen: facultatively anaerobic
(6) Optimum growth temperature: 37 to 40° C.
(7) Optimum growth pH: pH 5.5 to 5.8

2) Like strain #35 of this case and strain #58 of this case, strain #71 of this case is a *Lactobacillus salivarius* strain having 16S rRNA gene having the nucleotide sequence of SEQ ID NO: 1 and has similar features to those of strain #35 of this case and strain #58 of this case. That is, strain #71 of this case has the following features. Strain #71 of this case was deposited for an international deposit at NITE Patent Microorganisms Depositary (NPMD), National Institute of Technology and Evaluation (NITE) (address: #122, 2-5-8 Kazusakamatari, Kisarazu-shi, Chiba 292-0818, Japan) on May 19, 2020 under international deposit accession number NITE BP-03220.

(a) Cell Morphology

Shape: *bacillus*, sporulation: (−), motility: (−)

(b) Colony Morphology (The strain was smeared on an MRS agar plate and aerobically cultured at 37° C. for 24 hours, and the colony shape was observed.)

(1) Gram stain: (+)
(2) Gas production: (−)
(3) Catalase activity: (−)
(4) Indole production: (−)
(5) Response to oxygen: facultatively anaerobic
(6) Optimum growth temperature: 37 to 40° C.
(7) Optimum growth pH: pH 5.5 to 5.8

Example 12. Evaluation of Immunomodulatory Potential of Strain #131 of this Case on Double-Stranded RNA Model Virus To confirm that strain #131 of this case has the action of enhancing antiviral immune response like strain #35 of this case and strain #58 of this case, the PIE cell line was stimulated with strain #131 of this case before stimulation with poly I:C, and the expression of an antiviral factor was analyzed.

12-1 Method

The immune response of the cells was analyzed according to the following procedures [1] to [4].

[1] The PIE cell line was seeded in a 12-well plate coated with type I collagen (manufactured by Sumitomo Bakelite Co., Ltd.) at $3 \times 10^4$ cells/well and cultured in DMEM liquid medium for three days.

[2] Strain #131 of this case was added to the medium at $5.0 \times 10^7$ cells/mL per well, and the cells were cultured (stimulated) for 48 hours. As a control which was not stimulated with strain #131 of this case, the PIE cell line was cultured similarly in DMEM liquid medium which did not contain strain #131 of this case.

[3] The medium was removed, and the cells were washed twice with PBS. Then, the medium was replaced with DMEM liquid medium containing 50 ng/mL poly I:C (catalog number P9582, manufactured by SIGMA), and the cells were cultured for 12 hours and thus stimulated with poly I:C. As a control which was not stimulated with poly I:C, the PIE cell line was cultured similarly in poly I:C-free DMEM liquid medium.

[4] After removing the medium, the procedures from the collection of the total RNA of the cells to the analysis of the mRNA expression level of an antiviral factor (IFN-β) gene were conducted according to the procedures [3] to [5] in the section [Expression Analysis of Cytokine-Related Factors in Poly I:C-Stimulated PIE Cell Line] in Example 1 above. The expression level of IFN-β with the stimulation with strain #131 of this case (see FIG. 16) was calculated based on the equation ([the mRNA expression level of IFN-β gene/the mRNA expression level of β-actin gene] with the stimulation with strain #131 of this case before the stimulation with poly I:C/[the mRNA expression level of IFN-β gene/the mRNA expression level of β-actin gene] with the stimulation with poly I:C). As a control for comparison, the expression level of the antiviral factor without the stimulation with strain #131 of this case and poly I:C was also calculated (see FIG. 16).

4-2 Results

The expression level of IFN-β in the PIE cell line which was stimulated with strain #131 of this case before the stimulation with poly I:C increased significantly compared to the expression level in the PIE cell line which was not stimulated with strain #131 of this case and which was stimulated with poly I:C (see FIG. 16).

The results show that strain #131 of this case has the action of enhancing the expression of an antiviral factor like strain #35 of this case and strain #58 of this case. Moreover, because strain #35 of this case and strain #58 of this case as well as strain #131 of this case and strain #71 of this case are all *Lactobacillus salivarius* strains having 16S rRNA gene having the nucleotide sequence of SEQ ID NO: 1, it was suggested that a *Lactobacillus salivarius* strain having 16S rRNA gene having the nucleotide sequence of SEQ ID NO: 1 has both features of antiviral activity and the ability to assimilate wakame.

Example 13. Examination (2) of Viral Infection-Reducing Effect of *Lactobacillus* Strains of this Case It was analyzed whether *Lactobacillus* strains of a different species from *Lactobacillus salivarius* had an antiviral effect when the strains had a high sequence identity with the nucleotide sequence of 16S rRNA gene of *Lactobacillus salivarius* which exhibited an antiviral effect (namely, the nucleotide sequence of SEQ ID NO: 1). Specifically, a rotavirus infection test was conducted using nine *Lactobacillus plantarum* strains (strain #16 of this case, strain #6VG132 of this case, strain #6ML6109 of this case, strain #6ML686 of this case, strain #3CS123 of this case, strain #6VG141 of this case, strain #2CS82 of this case, strain #1FeB18 of this case and strain #4FeB195 of this case) which are included in the *Lactobacillus* strains of this case.

Strain #16 of this case is a *Lactobacillus plantarum* strain having 16S rRNA gene having the nucleotide sequence of SEQ ID NO: 52 and was deposited for an international deposit at NITE Patent Microorganisms Depositary (NPMD), National Institute of Technology and Evaluation (NITE) (address: #122, 2-5-8 Kazusakamatari, Kisarazu-shi, Chiba 292-0818, Japan) on Apr. 23, 2021 under international deposit accession number NITE BP-03474. Strain #16 of this case has the following features like the four *Lactobacillus salivarius* strains (strain #35 of this case, strain #58 of this case, strain #131 of this case and strain #71 of this case).

(a) Cell Morphology

Shape: bacillus, sporulation: (−), motility: (−)

(b) Colony Morphology (The strain was smeared on an MRS agar plate and aerobically cultured at 37° C. for 24 hours, and the colony shape was observed.)

(1) Gram stain: (+)

(2) Gas production: (−)

(3) Catalase activity: (−)

(4) Indole production: (−)

(5) Response to oxygen: facultatively anaerobic (6) Optimum growth temperature: 37 to 40° C.

(7) Optimum growth pH: pH 5.5 to 5.8

1) Strain #6ML686 of this case is a *Lactobacillus plantarum* strain having 16S rRNA gene having the nucleotide sequence of SEQ ID NO: 53 and was deposited for an international deposit at NITE Patent Microorganisms Depositary (NPMD), National Institute of Technology and Evaluation (NITE) (address: #122, 2-5-8 Kazusakamatari, Kisarazu-shi, Chiba 292-0818, Japan) on Apr. 23, 2021 under international deposit accession number NITE BP-03466. Strain #6ML686 of this case has the following features like the four *Lactobacillus salivarius* strains (strain #35 of this case, strain #58 of this case, strain #131 of this case and strain #71 of this case).

(a) Cell Morphology

Shape: bacillus, sporulation: (−), motility: (−)

(b) Colony Morphology (The strain was smeared on an MRS agar plate and aerobically cultured at 37° C. for 24 hours, and the colony shape was observed.)

(1) Gram stain: (+)

(2) Gas production: (−)

(3) Catalase activity: (−)

(4) Indole production: (−)

(5) Response to oxygen: facultatively anaerobic (6) Optimum growth temperature: 37 to 40° C.

(7) Optimum growth pH: pH 5.5 to 5.8

2) Strain #6ML6109 of this case is a *Lactobacillus plantarum* strain having 16S rRNA gene having the nucleotide sequence of SEQ ID NO: 53 and was deposited for an international deposit at NITE Patent Microorganisms Depositary (NPMD), National Institute of Technology and Evaluation (NITE) (address: #122, 2-5-8 Kazusakamatari, Kisarazu-shi, Chiba 292-0818, Japan) on Apr. 23, 2021 under international deposit accession number NITE BP-03468. Strain #6ML6109 of this case has the following features like the four *Lactobacillus salivarius* strains (strain #35 of this case, strain #58 of this case, strain #131 of this case and strain #71 of this case).

31

(a) Cell Morphology

Shape: bacillus, sporulation: (–), motility: (–)

(b) Colony Morphology (The strain was smeared on an MRS agar plate and aerobically cultured at 37° C. for 24 hours, and the colony shape was observed.)

(1) Gram stain: (+)

(2) Gas production: (–)

(3) Catalase activity: (–)

(4) Indole production: (–)

(5) Response to oxygen: facultatively anaerobic (6) Optimum growth temperature: 37 to 40° C.

(7) Optimum growth pH: pH 5.5 to 5.8

Strain #6VG132 of this case is a *Lactobacillus plantarum* strain having 16S rRNA gene having the nucleotide sequence of SEQ ID NO: 54 and was deposited for an international deposit at NITE Patent Microorganisms Depositary (NPMD), National Institute of Technology and Evaluation (NITE) (address: #122, 2-5-8 Kazusakamatari, Kisarazu-shi, Chiba 292-0818, Japan) on Apr. 23, 2021 under international deposit accession number NITE BP-03467. Strain #6VG132 of this case has the following features like the four *Lactobacillus salivarius* strains (strain #35 of this case, strain #58 of this case, strain #131 of this case and strain #71 of this case).

(a) Cell Morphology

Shape: bacillus, sporulation: (–), motility: (–)

(b) Colony Morphology (The strain was smeared on an MRS agar plate and aerobically cultured at 37° C. for 24 hours, and the colony shape was observed.)

(1) Gram stain: (+)

(2) Gas production: (–)

(3) Catalase activity: (–)

(4) Indole production: (–)

(5) Response to oxygen: facultatively anaerobic (6) Optimum growth temperature: 37 to 40° C.

(7) Optimum growth pH: pH 5.5 to 5.8

Strain #6VG141 of this case is a *Lactobacillus plantarum* strain having 16S rRNA gene having the nucleotide sequence of SEQ ID NO: 55 and was deposited for an international deposit at NITE Patent Microorganisms Depositary (NPMD), National Institute of Technology and Evaluation (NITE) (address: #122, 2-5-8 Kazusakamatari, Kisarazu-shi, Chiba 292-0818, Japan) on Apr. 23, 2021 under international deposit accession number NITE BP-03469. Strain #6VG141 of this case has the following features like the four *Lactobacillus salivarius* strains (strain #35 of this case, strain #58 of this case, strain #131 of this case and strain #71 of this case).

(a) Cell Morphology

Shape: bacillus, sporulation: (–), motility: (–)

(b) Colony Morphology (The strain was smeared on an MRS agar plate and aerobically cultured at 37° C. for 24 hours, and the colony shape was observed.)

(1) Gram stain: (+)

(2) Gas production: (–)

(3) Catalase activity: (–)

(4) Indole production: (–)

(5) Response to oxygen: facultatively anaerobic (6) Optimum growth temperature: 37 to 40° C.

(7) Optimum growth pH: pH 5.5 to 5.8

1) Strain #2CS82 of this case is a *Lactobacillus plantarum* strain having 16S rRNA gene having the nucleotide sequence of SEQ ID NO: 56 and was deposited for an international deposit at NITE Patent Microorganisms Depositary (NPMD), National Institute of Technology and Evaluation (NITE) (address: #122, 2-5-8 Kazusakamatari, Kisarazu-shi, Chiba 292-0818, Japan) on Apr. 23, 2021 under international deposit accession number NITE BP-03470. Strain #2CS82 of this case has the following features like the four *Lactobacillus salivarius* strains (strain #35 of this case, strain #58 of this case, strain #131 of this case and strain #71 of this case).

(a) Cell Morphology

Shape: bacillus, sporulation: (–), motility: (–)

(b) Colony Morphology (The strain was smeared on an MRS agar plate and aerobically cultured at 37° C. for 24 hours, and the colony shape was observed.)

(1) Gram stain: (+)

(2) Gas production: (–)

(3) Catalase activity: (–)

(4) Indole production: (–)

(5) Response to oxygen: facultatively anaerobic (6) Optimum growth temperature: 37 to 40° C.

(7) Optimum growth pH: pH 5.5 to 5.8

2) Strain #1FeB18 of this case is a *Lactobacillus plantarum* strain having 16S rRNA gene having the nucleotide sequence of SEQ ID NO: 56 and was deposited for an international deposit at NITE Patent Microorganisms Depositary (NPMD), National Institute of Technology and Evaluation (NITE) (address: #122, 2-5-8 Kazusakamatari, Kisarazu-shi, Chiba 292-0818, Japan) on Apr. 23, 2021 under international deposit accession number NITE BP-03472. Strain #1FeB18 of this case has the following features like the four *Lactobacillus salivarius* strains (strain #35 of this case, strain #58 of this case, strain #131 of this case and strain #71 of this case).

(a) Cell Morphology

Shape: bacillus, sporulation: (–), motility: (–)

(b) Colony Morphology (The strain was smeared on an MRS agar plate and aerobically cultured at 37° C. for 24 hours, and the colony shape was observed.)

(1) Gram stain: (+)

(2) Gas production: (–)

(3) Catalase activity: (–)

(4) Indole production: (–)

(5) Response to oxygen: facultatively anaerobic (6) Optimum growth temperature: 37 to 40° C.

(7) Optimum growth pH: pH 5.5 to 5.8

Strain #3CS123 of this case is a *Lactobacillus plantarum* strain having 16S rRNA gene having the nucleotide sequence of SEQ ID NO: 57 and was deposited for an international deposit at NITE Patent Microorganisms Depositary (NPMD), National Institute of Technology and Evaluation (NITE) (address: #122, 2-5-8 Kazusakamatari, Kisarazu-shi, Chiba 292-0818, Japan) on Apr. 23, 2021 under international deposit accession number NITE BP-03471. Strain #3CS123 of this case has the following features like the four *Lactobacillus salivarius* strains (strain #35 of this case, strain #58 of this case, strain #131 of this case and strain #71 of this case).

(a) Cell Morphology

Shape: bacillus, sporulation: (–), motility: (–)

(b) Colony Morphology (The strain was smeared on an MRS agar plate and aerobically cultured at 37° C. for 24 hours, and the colony shape was observed.)

(1) Gram stain: (+)

(2) Gas production: (–)

(3) Catalase activity: (–)

(4) Indole production: (–)

(5) Response to oxygen: facultatively anaerobic (6) Optimum growth temperature: 37 to 40° C.

(7) Optimum growth pH: pH 5.5 to 5.8

Strain #4FeB195 of this case is a *Lactobacillus mucosae* strain having 16S rRNA gene having the nucleotide sequence of SEQ ID NO: 58 and was deposited for an international deposit at NITE Patent Microorganisms Depositary (NPMD), National Institute of Technology and Evaluation (NITE) (address: #122, 2-5-8 Kazusakamatari, Kisarazu-shi, Chiba 292-0818, Japan) on Apr. 23, 2021 under international deposit accession number NITE BP-03473. Strain #4FeB195 of this case has the following features like the four *Lactobacillus salivarius* strains (strain #35 of this case, strain #58 of this case, strain #131 of this case and strain #71 of this case).

(a) Cell Morphology

Shape: bacillus, sporulation: (−), motility: (−)

(b) Colony Morphology (The strain was smeared on an MRS agar plate and aerobically cultured at 37° C. for 24 hours, and the colony shape was observed.)

(1) Gram stain: (+)

(2) Gas production: (−)

(3) Catalase activity: (−)

(4) Indole production: (−)

(5) Response to oxygen: facultatively anaerobic (6) Optimum growth temperature: 37 to 40° C.

(7) Optimum growth pH: pH 5.5 to 5.8

The nine *Lactobacillus plantarum* strains are all *Lactobacillus* strains having 16S rRNA gene having an identity of at least 90% with the nucleotide sequence of SEQ ID NO: 1.

13-1 Materials and Methods

[Material]

As the PIE1-3 cell line, cells cloned from the small intestine of a Duroc weanling piglet were used.

[Method]

The rotavirus infection test and the subsequent analysis of the rotavirus infection level and the rotavirus-infected cells were conducted according to the following procedures [1] to [7].

[1] The PIE1-3 cell line was seeded in 96-well plates coated with type I collagen (manufactured by Sumitomo Bakelite Co., Ltd.) at $3\times10^4$ cells/mL and cultured in DMEM liquid medium for eight days.

[2] The nine *Lactobacillus plantarum* strains were added to the medium each at 1 MOI per well, and the cells were strain #4FeB195 of this case), the procedures from fixing of the cells to the indirect fluorescent antibody assay were conducted (see FIG. 18) according to the procedures [4] to [7] in the section [Rotavirus Infection Test and Indirect Fluorescent Antibody Assay] in Example 6 above.

[5] Moreover, regarding the PIE1-3 cell line which was stimulated with seven *Lactobacillus plantarum* strains (strain #16 of this case, strain #6VG132 of this case, strain #6ML6109 of this case, strain #6ML686 of this case, strain #3CS123 of this case, strain #6VG141 of this case and strain #2CS82 of this case), the rotavirus infection levels were analyzed using the expression level of a rotavirus-derived gene as an indicator. First, after removing the active rotavirus solution, the cells were washed once with PBS, and the total RNA of the cells was obtained according to a standard method using a cell-dissolving solution (TRIZOL™ reagent [manufactured by Invitrogen]). The concentrations and the purities of the RNA were measured with NANODROP® ND-1000 spectrophotometer (manufactured by Thermo Fisher Scientific).

[6] cDNA was synthesized from the obtained total RNA using PRIMESCRIPT™ RT reagent Kit with gDNA Eraser (Perfect Real Time) (manufactured by Takara) according to the protocols attached to the product.

[7] To analyze the mRNA expression levels of a rotavirus-derived gene (NSP5 gene) and β-actin gene, quantitative PCR analysis was conducted using the synthesized cDNA as a template using the primer sets shown in Table 2 below (the sense primers and the antisense primers), PLATINUM™ SYBR™ Green qPCR Super Mix-UDG with ROX (manufactured by Invitrogen) and ABI PRISM 7300 real-time PCR system (manufactured by Applied Biosystem) according to the protocols attached to the product. The expression levels of NSP5 with the stimulation with the nine *Lactobacillus plantarum* strains were calculated based on the equation ([the mRNA expression level of NSP5 gene/the mRNA expression level of β-actin gene] with the stimulation with the nine *Lactobacillus plantarum* strains/[the mRNA expression level of NSP5 gene/the mRNA expression level of β-actin gene] without the stimulation with the nine *Lactobacillus plantarum* strains) (see FIG. 17).

TABLE 2

| Gene Name | Sense Primer (5'→3') | SEQ ID NO: | Antisense Primer (5'→3') | SEQ ID NO: |
|---|---|---|---|---|
| β-actin | TGGATAAGCTGCAGTCACAG | 2 | GCGTAGAGGTCCTCCCTGATGT | 3 |
| NSP5 | CTCTTTCTGGAAAATCTATTGGTAG | 59 | GATGAATCCATAGACACGCCAG | 60 | cultured (stimulated) for 48 hours. As a control which was not stimulated with the strains, the PIE1-3 cell line was cultured similarly in DMEM liquid medium which did not contain the strains.

[3] The cells were washed three times with FCS-free DMEM liquid medium, and the active rotavirus solution prepared according to the method described in the section [Preparation of Active Rotavirus Solution] in Example 6 above was added at 100 μL (corresponding to 1 MOI) per well, followed by incubation under the conditions of 5% $CO_2$/20% $O_2$ at 37° C. for 12 hours.

[4] After removing the active rotavirus solution, to analyze the percentages of the rotavirus-infected cells in the PIE1-3 cell line which was stimulated with two *Lactobacillus plantarum* strains (strain #1FeB18 of this case and 13-2 Results When the PIE1-3 cell line was stimulated with the seven *Lactobacillus plantarum* strains (strain #16 of this case, strain #6VG132 of this case, strain #6ML6109 of this case, strain #6ML686 of this case, strain #3CS123 of this case, strain #6VG141 of this case and strain #2CS82 of this case) before the incubation in the active rotavirus solution, the expression level of rotavirus-derived NSP5 decreased significantly compared to the case without the stimulation with the strains (see FIG. 17).

Moreover, it was shown that, when the PIE1-3 cell line was stimulated with the two *Lactobacillus plantarum* strains (strain #1FeB18 of this case and strain #4FeB195 of this case) before the incubation in the active rotavirus solution, the percentages of the rotavirus-infected cells decreased significantly compared to the case without the stimulation with the strains (see FIG. 18).

The results show that the nine *Lactobacillus plantarum* strains have the effect of reducing (preventing) viral infection.

INDUSTRIAL APPLICABILITY

The invention contributes to prevention or treatment of viral infection in livestock industry or human medicine.

---

The invention claimed is:

1. A method for preventing or treating rotavirus infection, comprising a step of administering to a subject in need of prevention or treatment of rotavirus infection one or more *Lactobacillus* strains selected from the group consisting of:

a *Lactobacillus salivarius* strain deposited under accession number NITE BP-03218;

a *Lactobacillus salivarius* strain deposited under accession number NITE BP-03219;

a *Lactobacillus salivarius* strain deposited under accession number NITE BP-03221;

a *Lactobacillus plantarum* strain deposited under accession number NITE BP-03466;

a *Lactobacillus plantarum* strain deposited under accession number NITE BP-03467;

a *Lactobacillus plantarum* strain deposited under accession number NITE BP-03468;

a *Lactobacillus plantarum* strain deposited under accession number NITE BP-03469;

a *Lactobacillus plantarum* strain deposited under accession number NITE BP-03470;

a *Lactobacillus plantarum* strain deposited under accession number NITE BP-03471;

a *Lactobacillus plantarum* strain deposited under accession number NITE BP-03472;

a *Lactobacillus plantarum* strain deposited under accession number NITE BP-03474; and a *Lactobacillus mucosae* strain deposited under accession number NITE BP-03473, wherein the administering of one or more *Lactobacillus* strains has an action of enhancing expression of an antiviral factor and/or an action of reducing expression of a down-regulator of an antiviral factor.

2. The method according to claim 1, wherein the antiviral factor is one, two or more antiviral factors selected from: interferon-β (IFN-β), interferon-λ (IFN-λ), MX dynamin like GTPase 1 (Mx1), 2'-5'-oligoadenylate synthetase 1 (OAS1), Ribonuclease L (RNaseL), Protein kinase R (PKR) and Retinoic acid inducible gene-I (RIG-I), and wherein the downregulator of an antiviral factor is one or two down-regulators of an antiviral factor selected from A20 and Toll-interacting protein (Tollip).

3. The method according to claim 2, wherein the *Lactobacillus plantarum* strain and the *Lactobacillus mucosae* strain have an action of enhancing expression of one, two or more receptors selected from TLR 2, TLR4 and NOD2.

4. The method according to claim 3, wherein the rotavirus is a double-stranded RNA virus.

5. The method according to claim 2, wherein the rotavirus is a double-stranded RNA virus.

6. The method according to claim 2, wherein the *Lactobacillus plantarum* strain and the *Lactobacillus mucosae* strain exhibits an ability to assimilate wakame.

7. The method according to claim 1, wherein the *Lactobacillus plantarum* strain and the *Lactobacillus mucosae* strain have an action of enhancing expression of one, two or more receptors selected from Toll-like receptor 2 (TLR2), Toll-like receptor 4 (TLR4) and Nucleotide binding oligomerization domain-like receptor 2 (NOD2).

8. The method according to claim 7, wherein the rotavirus is a double-stranded RNA virus.

9. The method according to claim 1, wherein the rotavirus is a double-stranded RNA virus.

10. The method according to claim 1, wherein the *Lactobacillus plantarum* strain and the *Lactobacillus mucosae* strain exhibits an ability to assimilate wakame.

11. The method according to claim 1, comprising administering to the subject the *Lactobacillus* strain as livestock feed or a food or a drink.

12. The method of claim 1, wherein the administering comprises administering any two or more of the *Lactobacillus* strains.

* * * * *

SEQUENCE LISTING

<160> NUMBER OF SEQ ID NOS: 60

<210> SEQ ID NO 1
<211> LENGTH: 1487
<212> TYPE: DNA
<213> ORGANISM: Lactobacillus sp.
<220> FEATURE:
<221> NAME/KEY: misc_feature
<223> OTHER INFORMATION: Inventor:KITAZAWA, Haruki; ASO, Hisashi;
      OHTSUBO, Wakako
<220> FEATURE:
<221> NAME/KEY: misc_feature
<223> OTHER INFORMATION: 16S rRNA of the present Lactobacillus bacteria
      strain

<400> SEQUENCE: 1

```
gacgaacgct ggcggcgtgc ctaatacatg caagtcgaac gaaactttct tacaccgaat      60
gcttgcattc accgtaagaa gttgagtggc ggacgggtga gtaacacgtg ggtaacctgc     120
ctaaaagaag gggataacac ttggaaacag gtgctaatac cgtatatctc taaggatcgc     180
atgatcctta gatgaaagat ggttctgcta tcgcttttag atggacccgc ggcgtattaa     240
ctagttggtg gggtaacggc ctaccaaggt gatgatacgt agccgaactg agaggttgat     300
cggccacatt gggactgaga cacggcccaa actcctacgg gaggcagcag tagggaatct     360
tccacaatgg acgcaagtct gatggagcaa cgccgcgtga gtgaagaagg tcttcggatc     420
gtaaaactct gttgttagag aagaacacga gtgagagtaa ctgttcattc gatgacggta     480
tctaaccagc aagtcacggc taactacgtg ccagcagccg cggtaatacg taggtggcaa     540
gcgttgtccg gatttattgg gcgtaaaggg aacgcaggcg gtcttttaag tctgatgtga     600
aagccttcgg cttaaccgga gtagtgcatt ggaaactgga agacttgagt gcagaagagg     660
agagtggaac tccatgtgta gcggtgaaat gcgtagatat atggaagaac accagtggcg     720
aaagcggctc tctggtctgt aactgacgct gaggttcgaa agcgtgggta gcaaacagga     780
ttagataccc tggtagtcca cgccgtaaac gatgaatgct aggtgttgga gggtttccgc     840
ccttcagtgc cgcagctaac gcaataagca ttccgcctgg ggagtacgac cgcaaggttg     900
aaactcaaag gaattgacgg gggcccgcac aagcggtgga gcatgtggtt taattcgaag     960
caacgcgaag aaccttacca ggtcttgaca tcctttgacc acctaagaga ttaggttttc    1020
ccttcgggga caaagtgaca ggtggtgcat ggctgtcgtc agctcgtgtc gtgagatgtt    1080
gggttaagtc ccgcaacgag cgcaaccctt gttgtcagtt gccagcatta agttgggcac    1140
tctggcgaga ctgccggtga caaaccggag gaaggtgggg acgacgtcaa gtcatcatgc    1200
cccttatgac ctgggctaca cacgtgctac aatggacggt acaacgagtc gcgagaccgc    1260
gaggtttagc taatctctta agccgttct cagttcggat tgtaggctgc aactcgccta    1320
catgaagtcg gaatcgctag taatcgcgaa tcagcatgtc gcggtgaata cgttcccggg    1380
ccttgtacac accgcccgtc acaccatgag agtttgtaac acccaaagcc ggtggggtaa    1440
ccgcaaggag ccagccgtct aaggtgggac agatgattgg ggtgaag                  1487
```

<210> SEQ ID NO 2
<211> LENGTH: 20
<212> TYPE: DNA

```
<213> ORGANISM: Artificial
<220> FEATURE:
<223> OTHER INFORMATION: beta-actin sense primer

<400> SEQUENCE: 2
tggataagct gcagtcacag                                            20

<210> SEQ ID NO 3
<211> LENGTH: 22
<212> TYPE: DNA
<213> ORGANISM: Artificial
<220> FEATURE:
<223> OTHER INFORMATION: beta-actin antisense primer

<400> SEQUENCE: 3
gcgtagaggt cctccctgat gt                                         22

<210> SEQ ID NO 4
<211> LENGTH: 20
<212> TYPE: DNA
<213> ORGANISM: Artificial
<220> FEATURE:
<223> OTHER INFORMATION: IFN-beta sense primer

<400> SEQUENCE: 4
agttgcctgg gactcctcaa                                            20

<210> SEQ ID NO 5
<211> LENGTH: 22
<212> TYPE: DNA
<213> ORGANISM: Artificial
<220> FEATURE:
<223> OTHER INFORMATION: IFN-beta antisense primer

<400> SEQUENCE: 5
cctcagggac ctcaaagttc at                                         22

<210> SEQ ID NO 6
<211> LENGTH: 25
<212> TYPE: DNA
<213> ORGANISM: Artificial
<220> FEATURE:
<223> OTHER INFORMATION: IFN-lambda sense primer

<400> SEQUENCE: 6
ccttagaggc tgagctagac ttgac                                      25

<210> SEQ ID NO 7
<211> LENGTH: 22
<212> TYPE: DNA
<213> ORGANISM: Artificial
<220> FEATURE:
<223> OTHER INFORMATION: IFN-lambda antisense primer

<400> SEQUENCE: 7
agcctgaagt tcgacgtgga tg                                         22

<210> SEQ ID NO 8
<211> LENGTH: 18
<212> TYPE: DNA
<213> ORGANISM: Artificial
<220> FEATURE:
<223> OTHER INFORMATION: Mx1 sense primer

<400> SEQUENCE: 8
gaggtggacc ccgaagga                                              18
```

```
<210> SEQ ID NO 9
<211> LENGTH: 18
<212> TYPE: DNA
<213> ORGANISM: Artificial
<220> FEATURE:
<223> OTHER INFORMATION: Mx1 antisense primer

<400> SEQUENCE: 9
caccagatcc ggcttcgt                                                 18

<210> SEQ ID NO 10
<211> LENGTH: 20
<212> TYPE: DNA
<213> ORGANISM: Artificial
<220> FEATURE:
<223> OTHER INFORMATION: OAS1 sense primer

<400> SEQUENCE: 10
ccaacaggtt cagacagcct                                               20

<210> SEQ ID NO 11
<211> LENGTH: 20
<212> TYPE: DNA
<213> ORGANISM: Artificial
<220> FEATURE:
<223> OTHER INFORMATION: OAS1 antisense primer

<400> SEQUENCE: 11
gaggagccac ccttcacaac                                               20

<210> SEQ ID NO 12
<211> LENGTH: 18
<212> TYPE: DNA
<213> ORGANISM: Artificial
<220> FEATURE:
<223> OTHER INFORMATION: RNaseL sense primer

<400> SEQUENCE: 12
gcagccgagc caacgata                                                 18

<210> SEQ ID NO 13
<211> LENGTH: 19
<212> TYPE: DNA
<213> ORGANISM: Artificial
<220> FEATURE:
<223> OTHER INFORMATION: RNaseL antisense primer

<400> SEQUENCE: 13
agctcccgtc gctctcact                                                19

<210> SEQ ID NO 14
<211> LENGTH: 20
<212> TYPE: DNA
<213> ORGANISM: Artificial
<220> FEATURE:
<223> OTHER INFORMATION: PKR sense primer

<400> SEQUENCE: 14
ccctgcactt ctagccatct                                               20

<210> SEQ ID NO 15
<211> LENGTH: 21
<212> TYPE: DNA
<213> ORGANISM: Artificial
<220> FEATURE:
```

<223> OTHER INFORMATION: PKR antisense primer

<400> SEQUENCE: 15
cgaccactgg ccatttcttt c                                                    21

<210> SEQ ID NO 16
<211> LENGTH: 20
<212> TYPE: DNA
<213> ORGANISM: Artificial
<220> FEATURE:
<223> OTHER INFORMATION: RIG-I sense primer

<400> SEQUENCE: 16
tatccgagca gcaggctttg                                                     20

<210> SEQ ID NO 17
<211> LENGTH: 22
<212> TYPE: DNA
<213> ORGANISM: Artificial
<220> FEATURE:
<223> OTHER INFORMATION: RIG-I antisense primer

<400> SEQUENCE: 17
ctcgttgctg ggatctatgg cc                                                  22

<210> SEQ ID NO 18
<211> LENGTH: 20
<212> TYPE: DNA
<213> ORGANISM: Artificial
<220> FEATURE:
<223> OTHER INFORMATION: TLR2 sense primer

<400> SEQUENCE: 18
acatgaagat gatgtgggcc                                                     20

<210> SEQ ID NO 19
<211> LENGTH: 20
<212> TYPE: DNA
<213> ORGANISM: Artificial
<220> FEATURE:
<223> OTHER INFORMATION: TLR2 antisense primer

<400> SEQUENCE: 19
taggagtcct gctcactgta                                                     20

<210> SEQ ID NO 20
<211> LENGTH: 20
<212> TYPE: DNA
<213> ORGANISM: Artificial
<220> FEATURE:
<223> OTHER INFORMATION: TLR3 sense primer

<400> SEQUENCE: 20
tagagacatg gattgctccc                                                     20

<210> SEQ ID NO 21
<211> LENGTH: 20
<212> TYPE: DNA
<213> ORGANISM: Artificial
<220> FEATURE:
<223> OTHER INFORMATION: TLR3 antisense primer

<400> SEQUENCE: 21
aacttctgga atgcaggtcc                                                     20

-continued

```
<210> SEQ ID NO 22
<211> LENGTH: 20
<212> TYPE: DNA
<213> ORGANISM: Artificial
<220> FEATURE:
<223> OTHER INFORMATION: TLR4 sense primer

<400> SEQUENCE: 22
ctctgccttc actacagaga                                               20

<210> SEQ ID NO 23
<211> LENGTH: 20
<212> TYPE: DNA
<213> ORGANISM: Artificial
<220> FEATURE:
<223> OTHER INFORMATION: TLR4 antisense primer

<400> SEQUENCE: 23
ctctgccttc actacagaga                                               20

<210> SEQ ID NO 24
<211> LENGTH: 20
<212> TYPE: DNA
<213> ORGANISM: Artificial
<220> FEATURE:
<223> OTHER INFORMATION: NOD1 sense primer

<400> SEQUENCE: 24
ctgtcgtcaa caccgatcca                                               20

<210> SEQ ID NO 25
<211> LENGTH: 19
<212> TYPE: DNA
<213> ORGANISM: Artificial
<220> FEATURE:
<223> OTHER INFORMATION: NOD1 antisense primer

<400> SEQUENCE: 25
ccagttggtg acgcagctt                                                19

<210> SEQ ID NO 26
<211> LENGTH: 22
<212> TYPE: DNA
<213> ORGANISM: Artificial
<220> FEATURE:
<223> OTHER INFORMATION: NOD2 sense primer

<400> SEQUENCE: 26
gagcgcatcc tcttaacttt cg                                            22

<210> SEQ ID NO 27
<211> LENGTH: 19
<212> TYPE: DNA
<213> ORGANISM: Artificial
<220> FEATURE:
<223> OTHER INFORMATION: NOD2 antisense primer

<400> SEQUENCE: 27
acgctcgtga tccgtgaac                                                19

<210> SEQ ID NO 28
<211> LENGTH: 22
<212> TYPE: DNA
<213> ORGANISM: Artificial
<220> FEATURE:
<223> OTHER INFORMATION: MCP-1 sense primer
```

-continued

```
<400> SEQUENCE: 28
acagaagagt caccagcagc aa                                            22

<210> SEQ ID NO 29
<211> LENGTH: 16
<212> TYPE: DNA
<213> ORGANISM: Artificial
<220> FEATURE:
<223> OTHER INFORMATION: MCP-1 antisense primer

<400> SEQUENCE: 29
gcccgcgatg gtcttg                                                  16

<210> SEQ ID NO 30
<211> LENGTH: 20
<212> TYPE: DNA
<213> ORGANISM: Artificial
<220> FEATURE:
<223> OTHER INFORMATION: IL-6 sense primer

<400> SEQUENCE: 30
tccataagct gcagtcacag                                              20

<210> SEQ ID NO 31
<211> LENGTH: 20
<212> TYPE: DNA
<213> ORGANISM: Artificial
<220> FEATURE:
<223> OTHER INFORMATION: IL-6 antisense primer

<400> SEQUENCE: 31
attatccgaa tggccctcag                                              20

<210> SEQ ID NO 32
<211> LENGTH: 21
<212> TYPE: DNA
<213> ORGANISM: Artificial
<220> FEATURE:
<223> OTHER INFORMATION: IL-8 sense primer

<400> SEQUENCE: 32
gctctctgtg aggctgcagt t                                            21

<210> SEQ ID NO 33
<211> LENGTH: 22
<212> TYPE: DNA
<213> ORGANISM: Artificial
<220> FEATURE:
<223> OTHER INFORMATION: IL-8 antisense primer

<400> SEQUENCE: 33
tttatgcact ggcatcgaag tt                                           22

<210> SEQ ID NO 34
<211> LENGTH: 20
<212> TYPE: DNA
<213> ORGANISM: Artificial
<220> FEATURE:
<223> OTHER INFORMATION: IL-12 sense primer

<400> SEQUENCE: 34
agttccaggc catgaatgca                                              20

<210> SEQ ID NO 35
<211> LENGTH: 20
```

-continued

<212> TYPE: DNA
<213> ORGANISM: Artificial
<220> FEATURE:
<223> OTHER INFORMATION: IL-12 antisense primer

<400> SEQUENCE: 35
tggcacagtc tcactgttga                                                        20

<210> SEQ ID NO 36
<211> LENGTH: 24
<212> TYPE: DNA
<213> ORGANISM: Artificial
<220> FEATURE:
<223> OTHER INFORMATION: IL-18 sense primer

<400> SEQUENCE: 36
tgaaccggaa gacaattgca tcag                                                   24

<210> SEQ ID NO 37
<211> LENGTH: 25
<212> TYPE: DNA
<213> ORGANISM: Artificial
<220> FEATURE:
<223> OTHER INFORMATION: IL-18 antisense primer

<400> SEQUENCE: 37
ccaggtcttc atcgttttca gctac                                                  25

<210> SEQ ID NO 38
<211> LENGTH: 20
<212> TYPE: DNA
<213> ORGANISM: Artificial
<220> FEATURE:
<223> OTHER INFORMATION: TNFalpha sense primer

<400> SEQUENCE: 38
cgactcagtg ccgagatcaa                                                        20

<210> SEQ ID NO 39
<211> LENGTH: 20
<212> TYPE: DNA
<213> ORGANISM: Artificial
<220> FEATURE:
<223> OTHER INFORMATION: TNFalpha antisense primer

<400> SEQUENCE: 39
cctgcccaga ttcagcaaag                                                        20

<210> SEQ ID NO 40
<211> LENGTH: 19
<212> TYPE: DNA
<213> ORGANISM: Artificial
<220> FEATURE:
<223> OTHER INFORMATION: A20 sense primer

<400> SEQUENCE: 40
cctccctgga aagccagaa                                                         19

<210> SEQ ID NO 41
<211> LENGTH: 21
<212> TYPE: DNA
<213> ORGANISM: Artificial
<220> FEATURE:
<223> OTHER INFORMATION: A20 antisense primer

<400> SEQUENCE: 41
gtgccacaag cttcctcact t                                      21

<210> SEQ ID NO 42
<211> LENGTH: 19
<212> TYPE: DNA
<213> ORGANISM: Artificial
<220> FEATURE:
<223> OTHER INFORMATION: BCL-3 sense primer

<400> SEQUENCE: 42
cgacgcggtg gacattaag                                         19

<210> SEQ ID NO 43
<211> LENGTH: 23
<212> TYPE: DNA
<213> ORGANISM: Artificial
<220> FEATURE:
<223> OTHER INFORMATION: BCL-3 antisense primer

<400> SEQUENCE: 43
accatgctaa ggctgttgtt ttc                                    23

<210> SEQ ID NO 44
<211> LENGTH: 17
<212> TYPE: DNA
<213> ORGANISM: Artificial
<220> FEATURE:
<223> OTHER INFORMATION: Tollip sense primer

<400> SEQUENCE: 44
taccgtgggc cgtctca                                           17

<210> SEQ ID NO 45
<211> LENGTH: 21
<212> TYPE: DNA
<213> ORGANISM: Artificial
<220> FEATURE:
<223> OTHER INFORMATION: Tollip antisense primer

<400> SEQUENCE: 45
ccgtagttct tcgccaactt g                                      21

<210> SEQ ID NO 46
<211> LENGTH: 20
<212> TYPE: DNA
<213> ORGANISM: Artificial
<220> FEATURE:
<223> OTHER INFORMATION: IRAK-M sense primer

<400> SEQUENCE: 46
tggagcagcc ttgaatcctt                                        20

<210> SEQ ID NO 47
<211> LENGTH: 23
<212> TYPE: DNA
<213> ORGANISM: Artificial
<220> FEATURE:
<223> OTHER INFORMATION: IRAK-M antisense primer

<400> SEQUENCE: 47
tggataacac gtttgggaat ctt                                    23

<210> SEQ ID NO 48
<211> LENGTH: 20
<212> TYPE: DNA
<213> ORGANISM: Artificial

-continued

```
<220> FEATURE:
<223> OTHER INFORMATION: MKP-1 sense primer

<400> SEQUENCE: 48
aacgagggtc aggctttttcc                                              20

<210> SEQ ID NO 49
<211> LENGTH: 21
<212> TYPE: DNA
<213> ORGANISM: Artificial
<220> FEATURE:
<223> OTHER INFORMATION: MKP-1 antisense primer

<400> SEQUENCE: 49
tccccaatgt gctgagttca g                                             21

<210> SEQ ID NO 50
<211> LENGTH: 22
<212> TYPE: DNA
<213> ORGANISM: Artificial
<220> FEATURE:
<223> OTHER INFORMATION: SIGIRR sense primer

<400> SEQUENCE: 50
atgtgaagtg tcggctcaat gt                                            22

<210> SEQ ID NO 51
<211> LENGTH: 22
<212> TYPE: DNA
<213> ORGANISM: Artificial
<220> FEATURE:
<223> OTHER INFORMATION: SIGIRR antisense primer

<400> SEQUENCE: 51
ttcatctcca cctccccata ct                                            22

<210> SEQ ID NO 52
<211> LENGTH: 1492
<212> TYPE: DNA
<213> ORGANISM: Lactobacillus sp.
<220> FEATURE:
<221> NAME/KEY: misc_feature
<223> OTHER INFORMATION: 16S rRNA of the present Lactobacillus bacteria
      strain #16

<400> SEQUENCE: 52
gacgaacgct ggcggcgtgc ctaatacatg caagtcgaac gaactctggt aatgattggt     60
gcttgcatca tgaattacat ttgagtgagt ggcgaactgg tgagtaacac gtgggaaacc    120
tgcccagaag cgggggataa cacctggaaa cagatgctaa taccgcataa caacttggac    180
cgcatggtcc gagtttgaaa gatggcttcg gctatcactt ttggatggtc ccgcggcgta    240
ttagctagat ggtgaggtaa cggctcacca tggcaatgat acgtagccga cctgagaggg    300
taatcggcca cattgggact gagacacggc ccaaactcct acgggaggca gcagtaggga    360
atcttccaca atggacgaaa gtctgatgga gcaacgccgc gtgagtgaag aagggtttcg    420
gctcgtaaaa ctctgttgtt aaagaagaac atatctgaga gtaactgttc aggtattgac    480
ggtatttaac cagaaagcca cggctaacta cgtgccagca gccgcggtaa tacgtaggtg    540
gcaagcgttg tccggattta ttgggcgtaa agcgagcgca ggcggttttt taagtctgat    600
gtgaaagcct tcggctcaac cgaagaagtg catcggaaac tgggraactt gagtgcagaa    660
gaggacagtg gaactccatg tgtagcggtg aaatgcgtag atatatggaa gaacaccagt    720
```

-continued

```
ggcgaaggcg gctgtctggt ctgtaactga cgctgaggct cgaaagtatg ggtagcaaac        780
aggattagat accctggtag tccataccgt aaacgatgaa tgctaagtgt tggagggttt        840
ccgcccttca gtgctgcagc taacgcatta agcattccgc ctggggagta cggccgcaag        900
gctgaaactc aaaggaattg acgggggccc gcacaagcgg tggagcatgt ggtttaattc        960
gaagctacgc gaagaacctt accaggtctt gacatactat gcaaatctaa gagattagac       1020
gttcccttcg gggacatgga tacaggtggt gcatggttgt cgtcagctcg tgtcgtgaga       1080
tgttgggtta agtcccgcaa cgagcgcaac ccttattatc agttgccagc attaagttgg       1140
gcactctggt gagactgccg gtgacaaacc ggaggaaggt ggggatgacg tcaaatcatc       1200
atgcccctta tgacctgggc tacacacgtg ctacaatgga tggtacaacg agttgcgaac       1260
tcgcgagagt aagctaatct cttaaagcca ttctcagttc ggattgtagg ctgcaactcg       1320
cctacatgaa gtcggaatcg ctagtaatcg cggatcagca tgccgcggtg aatacgttcc       1380
cgggccttgt acacaccgcc cgtcacacca tgagagtttg taacacccaa agtcggtggg       1440
gtaacctttt aggaaccagc cgcctaaggt gggacagatg attagggtga ag              1492
```

```
<210> SEQ ID NO 53
<211> LENGTH: 1492
<212> TYPE: DNA
<213> ORGANISM: Lactobacillus sp.
<220> FEATURE:
<221> NAME/KEY: misc_feature
<223> OTHER INFORMATION: 16S rRNA of the present Lactobacillus bacteria
      strain #6ML686 and #6ML6109

<400> SEQUENCE: 53
```

```
gacgaacgct ggcggcgtgc ctaatacatg caagtcgaac gaactctggt attgattggt         60
gcttgcatca tgatttacat ttgagtgagt ggcgaactgg tgagtaacac gtgggaaacc        120
tgcccagaag cggggggataa cacctggaaa cagatgctaa taccgcataa caacttggac        180
cgcatggtcc gagtttgaaa gatggcttcg gctatcactt ytggatggtc ccgcggcgta        240
ttagctagat ggtgaggtaa cggctcacca tggcaatgat acgtagccga cctgagaggg        300
taatcggcca cattgggact gagacacggc ccaaactcct acgggaggca gcagtaggga        360
atcttccaca atggacgaaa gtctgatgga gcaacgccgc gtgagtgaag aagggtttcg        420
gctcgtaaaa ctctgttgtt aaagaagaac atatctgaga gtaactgttc aggtattgac        480
ggtatttaac cagaaagcca cggctaacta cgtgccagca gccgcggtaa tacgtaggtg        540
gcaagcgttg tccggattta ttgggcgtaa agcgagcgca ggcggttttt taagtctgat        600
gtgaaagcct tcggctcaac cgaagaagtg catcggaaac tgggaaactt gagtgcagaa        660
gaggacagtg gaactccatg tgtagcggtg aaatgcgtag atatatggaa gaacaccagt        720
ggcgaaggcg gctgtctggt ctgtaactga cgctgaggct cgaaagtatg ggtagcaaac        780
aggattagat accctggtag tccataccgt aaacgatgaa tgctaagtgt tggagggttt        840
ccgcccttca gtgctgcagc taacgcatta agcattccgc ctggggagta cggccgcaag        900
gctgaaactc aaaggaattg acgggggccc gcacaagcgg tggagcatgt ggtttaattc        960
gaagctacgc gaagaacctt accaggtctt gacatactat gcaaatctaa gagattagac       1020
gttcccttcg gggacatgga tacaggtggt gcatggttgt cgtcagctcg tgtcgtgaga       1080
tgttgggtta agtcccgcaa cgagcgcaac ccttattatc agttgccagc attaagttgg       1140
gcactctggt gagactgccg gtgacaaacc ggaggaaggt ggggatgacg tcaaatcatc       1200
atgcccctta tgacctgggc tacacacgtg ctacaatgga tggtacaacg agttgcgaac       1260
```

```
tcgcgagagt aagctaatct cttaaagcca ttctcagttc ggattgtagg ctgcaactcg    1320
cctacatgaa gtcggaatcg ctagtaatcg cggatcagca tgccgcggtg aatacgttcc    1380
cgggccttgt acacaccgcc cgtcacacca tgagagtttg taacacccaa agtcggtggg    1440
gtaacctttt aggaaccagc cgcctaaggt gggacagatg attagggtga ag            1492
```

<210> SEQ ID NO 54
<211> LENGTH: 1492
<212> TYPE: DNA
<213> ORGANISM: Lactobacillus sp.
<220> FEATURE:
<221> NAME/KEY: misc_feature
<223> OTHER INFORMATION: 16S rRNA of the present Lactobacillus bacteria
     strain #6VG132

<400> SEQUENCE: 54

```
gacgaacgct ggcggcgtgc ctaatacatg caagtcgaac gaactctggt attgattggt      60
gcttgcatca tgatttacat ttgagtgagt ggcgaactgg tgagtaacac gtgggaaacc     120
tgcccagaag cggggggataa cacctggaaa cagatgctaa taccgcataa caacttggac    180
cgcatggtcc gagyttgaaa gatggcttcg gctatcactt ttggatggtc ccgcggcgta     240
ttagctagat ggtgrggtaa cggctcacca tggcaatgat acgtagccga cctgagaggg     300
taatcggcca cattgggact gagacacggc ccaaactcct acgggaggca gcagtaggga     360
atcttccaca atggacgaaa gtctgatgga gcaacgccgc gtgagtgaag aagggtttcg     420
gctcgtaaaa ctctgttgtt aaagaagaac atatctgaga gtaactgttc aggtattgac     480
ggtatttaac cagaaagcca cggctaacta cgtgccagca gccgcggtaa tacgtaggtg     540
gcaagcgttg tccggattta ttgggcgtaa agcgagcgca ggcggttttt taagtctgat     600
gtgaaagcct tcggctcaac cgaagaagtg catcggaaac tgggaaactt gagtgcagaa     660
gaggacagtg gaactccatg tgtagcggtg aaatgcgtag atatatggaa gaacaccagt     720
ggcgaaggcg gctgtctggt ctgtaactga cgctgaggct cgaaagtatg ggtagcaaac     780
aggattagat accctggtag tccataccgt aaacgatgaa tgctaagtgt tggagggttt     840
ccgcccttca gtgctgcagc taacgcatta agcattccgc ctggggagta cggccgcaag     900
gctgaaactc aaaggaattg acggggcccc gcacaagcgg tggagcatgt ggtttaattc     960
gaagctacgc gaagaacctt accaggtctt gacatactat gcaaatctaa gagattagac    1020
gttcccttcg gggacatgga tacaggtggt gcatggttgt cgtcagctcg tgtcgtgaga    1080
tgttgggtta agtcccgcaa cgagcgcaac ccttattatc agttgccagc attaagttgg    1140
gcactctggt gagactgccg gtgacaaacc ggaggaaggt ggggatgacg tcaaatcatc    1200
atgcccctta tgacctgggc tacacacgtg ctacaatgga tggtacaacg agttgcgaac    1260
tcgcgagagt aagctaatct cttaaagcca ttctcagttc ggattgtagg ctgcaactcg    1320
cctacatgaa gtcggaatcg ctagtaatcg cggatcagca tgccgcggtg aatacgttcc    1380
cgggccttgt acacaccgcc cgtcacacca tgagagtttg taacacccaa agtcggtggg    1440
gtaacctttt aggaaccagc cgcctaaggt gggacagatg attagggtga ag            1492
```

<210> SEQ ID NO 55
<211> LENGTH: 1492
<212> TYPE: DNA
<213> ORGANISM: Lactobacillus sp.
<220> FEATURE:
<221> NAME/KEY: misc_feature
<223> OTHER INFORMATION: 16S rRNA of the present Lactobacillus bacteria -continued

```
        strain #6VG141

<400> SEQUENCE: 55
gacgaacgct ggcggcgtgc ctaatacatg caagtcgaac gaactctggt attgattggt        60
gcttgcatca tgatttacat ttgagtgagt ggcgaactgg tgagtaacac gtgggaaacc       120
tgcccagaag cggggggataa cacctggaaa cagatgctaa taccgcataa caacttggac       180
cgcatggtcc gagtttgaaa gatggcttcg gctatcactt ctggatggtc ccgcggcgta       240
ttagctagat ggtgaggtaa cggctcacca tggcaatgat acgtagccga cctgagaggg       300
taatcggcca cattgggact gagacacggc ccaaactcct acgggaggca gcagtaggga       360
atcttccaca atggacgaaa gtctgatgga gcaacgccgc gtgagtgaag aagggtttcg       420
gctcgtaaaa ctctgttgtt aaagaagaac atatctgaga gtaactgttc aggtattgac       480
ggtatttaac cagaaagcca cggctaacta cgtgccagca gccgcggtaa tacgtaggtg       540
gcaagcgttg tccggattta ttgggcgtaa agcgagcgca ggcggttttt taagtctgat       600
gtgaaagcct tcggctcaac cgaagaagtg catcggaaac tgggaaactt gagtgcagaa       660
gaggacagtg gaactccatg tgtagcggtg aaatgcgtag atatatggaa gaacaccagt       720
ggcgaaggcg gctgtctggt ctgtaactga cgctgaggct cgaaagtatg ggtagcaaac       780
aggattagat accctggtag tccataccgt aaacgatgaa tgctaagtgt tggagggttt       840
ccgcccttca gtgctgcagc taacgcatta agcattccgc ctggggagta cggccgcaag       900
gctgaaactc aaaggaattg acggggggccc gcacaagcgg tggagcatgt ggtttaattc       960
gaagctacgc gaagaacctt accaggtctt gacatactat gcaaatctaa gagattagac      1020
gttcccttcg gggacatgga tacaggtggt gcatggttgt cgtcagctcg tgtcgtgaga      1080
tgttgggtta agtcccgcaa cgagcgcaac ccttattatc agttgccagc attaagttgg      1140
gcactctggt gagactgccg gtgacaaacc ggaggaaggt ggggatgacg tcaaatcatc      1200
atgcccctta tgacctgggc tacacacgtg ctacaatgga tggtacaacg agttgcgaac      1260
tcgcgagagt aagctaatct cttaaagcca ttctcagttc ggattgtagg ctgcaactcg      1320
cctacatgaa gtcggaatcg ctagtaatcg cggatcagca tgccgcggtg aatacgttcc      1380
cgggccttgt acacaccgcc cgtcacacca tgagagtttg taacacccaa agtcggtggg      1440
gtaacctttt aggaaccagc cgcctaaggt gggacagatg attagggtga ag              1492
```

<210> SEQ ID NO 56
<211> LENGTH: 1492
<212> TYPE: DNA
<213> ORGANISM: Lactobacillus sp.
<220> FEATURE:
<221> NAME/KEY: misc_feature
<223> OTHER INFORMATION: 16S rRNA of the present Lactobacillus bacteria
      strain #2CS82 and #1FeB18

```
<400> SEQUENCE: 56
gacgaacgct ggcggcgtgc ctaatacatg caagtcgaac gaactctggt attgattggt        60
gcttgcatca tgatttacat ttgagtgagt ggcgaactgg tgagtaacac gtgggaaacc       120
tgcccagaag cggggggataa cacctggaaa cagatgctaa taccgcataa caacttggac       180
cgcatggtcc gagcttgaaa gatggcttcg gctatcactt ttggatggtc ccgcggcgta       240
ttagctagat ggtggggtaa cggctcacca tggcaatgat acgtagccga cctgagaggg       300
taatcggcca cattgggact gagacacggc ccaaactcct acgggaggca gcagtaggga       360
atcttccaca atggacgaaa gtctgatgga gcaacgccgc gtgagtgaag aagggtttcg       420
```

```
gctcgtaaaa ctctgttgtt aaagaagaac atatctgaga gtaactgttc aggtattgac      480
ggtatttaac cagaaagcca cggctaacta cgtgccagca gccgcggtaa tacgtaggtg      540
gcaagcgttg tccggattta ttgggcgtaa agcgagcgca ggcggttttt taagtctgat      600
gtgaaagcct tcggctcaac cgaagaagtg catcggaaac tgggaaactt gagtgcagaa      660
gaggacagtg gaactccatg tgtagcggtg aaatgcgtag atatatggaa gaacaccagt      720
ggcgaaggcg gctgtctggt ctgtaactga cgctgaggct cgaaagtatg ggtagcaaac      780
aggattagat accctggtag tccataccgt aaacgatgaa tgctaagtgt tggagggttt      840
ccgcccttca gtgctgcagc taacgcatta agcattccgc ctggggagta cggccgcaag      900
gctgaaactc aaaggaattg acggggggccc gcacaagcgg tggagcatgt ggtttaattc      960
gaagctacgc gaagaacctt accaggtctt gacatactat gcaaatctaa gagattagac     1020
gttcccttcg gggacatgga tacaggtggt gcatggttgt cgtcagctcg tgtcgtgaga     1080
tgttgggtta agtcccgcaa cgagcgcaac ccttattatc agttgccagc attaagttgg     1140
gcactctggt gagactgccg gtgacaaacc ggaggaaggt ggggatgacg tcaaatcatc     1200 atgccccta tgacctgggc tacacacgtg ctacaatgga tggtacaacg agttgcgaac     1260
tcgcgagagt aagctaatct cttaaagcca ttctcagttc ggattgtagg ctgcaactcg     1320
cctacatgaa gtcggaatcg ctagtaatcg cggatcagca tgccgcggtg aatacgttcc     1380
cgggccttgt acacaccgcc cgtcacacca tgagagtttg taacacccaa agtcggtggg     1440
gtaacctttt aggaaccagc cgcctaaggt gggacagatg attagggtga ag           1492
```

```
<210> SEQ ID NO 57
<211> LENGTH: 1492
<212> TYPE: DNA
<213> ORGANISM: Lactobacillus sp.
<220> FEATURE:
<221> NAME/KEY: misc_feature
<223> OTHER INFORMATION: 16S rRNA of the present Lactobacillus bacteria
      strain #3CS123

<400> SEQUENCE: 57
```

```
gacgaacgct ggcggcgtgc ctaatacatg caagtcgaac gaactctggt attgattggt       60
gcttgcatca tgatttacat ttgagtgagt ggcgaactgg tgagtaacac gtgggaaacc      120
tgcccagaag cggggggataa cacctggaaa cagatgctaa taccgcataa caacttggac      180
cgcatggtcc gagtttgaaa gatggcttcg gctatcactt ttggatggtc ccgcggcgta      240
ttagctagat ggtgrggtaa cggctcacca tggcaatgat acgtagccga cctgagaggg      300
taatcggcca cattgggact gagacacggc ccaaactcct acgggaggca gcagtaggga      360
atcttccaca atggacgaaa gtctgatgga gcaacgccgc gtgagtgaag aagggtttcg      420
gctcgtaaaa ctctgttgtt aaagaagaac atatctgaga gtaactgttc aggtattgac      480
ggtatttaac cagaaagcca cggctaacta cgtgccagca gccgcggtaa tacgtaggtg      540
gcaagcgttg tccggattta ttgggcgtaa agcgagcgca ggcggttttt taagtctgat      600
gtgaaagcct tcggctcaac cgaagaagtg catcggaaac tgggaaactt gagtgcagaa      660
gaggacagtg gaactccatg tgtagcggtg aaatgcgtag atatatggaa gaacaccagt      720
ggcgaaggcg gctgtctggt ctgtaactga cgctgaggct cgaaagtatg ggtagcaaac      780
aggattagat accctggtag tccataccgt aaacgatgaa tgctaagtgt tggagggttt      840
ccgcccttca gtgctgcagc taacgcatta agcattccgc ctggggagta cggccgcaag      900
```

```
gctgaaactc aaaggaattg acggggggccc gcacaagcgg tggagcatgt ggtttaattc        960
gaagctacgc gaagaacctt accaggtctt gacatactat gcaaatctaa gagattagac       1020
gttcccttcg gggacatgga tacaggtggt gcatggttgt cgtcagctcg tgtcgtgaga       1080
tgttgggtta agtcccgcaa cgagcgcaac ccttattatc agttgccagc attaagttgg       1140
gcactctggt gagactgccg gtgacaaacc ggaggaaggt ggggatgacg tcaaatcatc       1200
atgcccctta tgacctgggc tacacacgtg ctacaatgga tggtacaacg agttgcgaac       1260
tcgcgagagt aagctaatct cttaaagcca ttctcagttc ggattgtagg ctgcaactcg       1320
cctacatgaa gtcggaatcg ctagtaatcg cggatcagca tgccgcggtg aatacgttcc       1380
cgggccttgt acacaccgcc cgtcacacca tgagagtttg taacacccaa agtcggtggg       1440
gtaacctttt aggaaccagc cgcctaaggt gggacagatg attagggtga ag              1492
```

<210> SEQ ID NO 58
<211> LENGTH: 1502
<212> TYPE: DNA
<213> ORGANISM: Lactobacillus sp.
<220> FEATURE:
<221> NAME/KEY: misc_feature
<223> OTHER INFORMATION: 16S rRNA of the present Lactobacillus bacteria
      strain #4FeB195

<400> SEQUENCE: 58

```
gatgaacgcc ggcggtgtgc ctaatacatg caagtcgaac gcgttggccc aactgattga         60
acgtgcttgc acggacttga cgttggttta ccagcgagtg gcggacgggt gagtaacacg        120
taggtaacct gccccaaagc gggggataac atttggaaac agatgctaat accgcataac        180
aatttgaatc gcatgattca aatttaaaag atggcttcgg ctatcacttt gggatggacc        240
tgcggcgcat tagcttgttg gtagggtaac ggcctaccaa ggctgtgatg cgtagccgag        300
ttgagagact gatcggccac aatggaactg agacacggtc catactccta cgggaggcag        360
cagtagggaa tcttccacaa tgggcgcaag cctgatggag caacaccgcg tgagtgaaga        420
agggtttcgg ctcgtaaagc tctgttgtta gagaagaacg tgcgtgagag caactgttca        480
cgcagtgacg gtatctaacc agaaagtcac ggctaactac gtgccagcag ccgcggtaat        540
acgtaggtgg caagcgttat ccggatttat tgggcgtaaa gcgagcgcag gcggtttgat        600
aagtctgatg tgaaagcctt tggcttaacc aaagaagtgc atcggaaact gtcagacttg        660
agtgcagaag aggacagtgg aactccatgt gtagcggtgg aatgcgtaga tatatggaag        720
aacaccagtg gcgaaggcgg ctgtctggtc tgcaactgac gctgaggctc gaaagcatgg        780
gtagcgaaca ggattagata ccctggtagt ccatgccgta aacgatgagt gctaggtgtt        840
ggagggtttc cgcccttcag tgccgcagct aacgcattaa gcactccgcc tggggagtac        900
gaccgcaagg ttgaaactca aaggaattga cggggggccg cacaagcggt ggagcatgtg        960
gtttaattcg aagctacgcg aagaacctta ccaggtcttg acatcttgcg ccaaccctag       1020
agatagggcg tttccttcgg gaacgcaatg acaggtggtg catggtcgtc gtcagctcgt       1080
gtcgtgagat gttgggttaa gtcccgcaac gagcgcaacc cttgttacta gttgccagca       1140
ttcagttggg cactctagtg agactgccgg tgacaaaccg gaggaaggtg gggacgacgt       1200
cagatcatca tgcccttat gacctgggct acacacgtgc tacaatggac ggtacaacga       1260
gtcgcgaact cgcgagggca agctaatctc ttaaaaccgt tctcagttcg gactgcaggc       1320
tgcaactcgc ctgcacgaag tcggaatcgc tagtaatcgc ggatcagcat gccgcggtga       1380
atacgttccc gggccttgta cacaccgccc gtcacaccat gagagtttgc aacacccaaa       1440
```

-continued

```
gtcggtgggg taacccttcg gggagctagc cgcctaaggt ggggcagatg attagggtga    1500
ag                                                                   1502

<210> SEQ ID NO 59
<211> LENGTH: 25
<212> TYPE: DNA
<213> ORGANISM: Artificial
<220> FEATURE:
<223> OTHER INFORMATION: NSP5 sense primer

<400> SEQUENCE: 59
ctctttctgg aaaatctatt ggtag                                            25

<210> SEQ ID NO 60
<211> LENGTH: 22
<212> TYPE: DNA
<213> ORGANISM: Artificial
<220> FEATURE:
<223> OTHER INFORMATION: NSP5 antisense primer

<400> SEQUENCE: 60
gatgaatcca tagacacgcc ag                                               22
```